(12) United States Patent
Ross et al.

(10) Patent No.: US 8,470,559 B2
(45) Date of Patent: Jun. 25, 2013

(54) GROWTH HORMONE FUSION PROTEINS

(75) Inventors: Richard Ross, Sheffield (GB); Peter Artymiuk, Sheffield (GB); Jon Sayers, Chesterfield (GB)

(73) Assignee: Asterion Limited, Sheffield (GB)

( * ) Notice: Subject to any disclaimer, the term of this patent is extended or adjusted under 35 U.S.C. 154(b) by 0 days.

(21) Appl. No.: 13/620,004

(22) Filed: Sep. 14, 2012

(65) Prior Publication Data

US 2013/0023477 A1    Jan. 24, 2013

Related U.S. Application Data

(62) Division of application No. 12/669,451, filed as application No. PCT/GB2008/002406 on Jul. 16, 2008, now Pat. No. 8,293,709.

(60) Provisional application No. 60/951,122, filed on Jul. 20, 2007.

(30) Foreign Application Priority Data

Sep. 14, 2007   (GB) .................................. 0717985.6

(51) Int. Cl.
| | |
|---|---|
| *A61K 38/27* | (2006.01) |
| *C07K 14/61* | (2006.01) |
| *C07K 14/72* | (2006.01) |
| *C12N 15/18* | (2006.01) |
| *C12N 1/21* | (2006.01) |
| *C12N 5/10* | (2006.01) |
| *C12N 15/63* | (2006.01) |

(52) U.S. Cl.
USPC ....... 435/69.4; 435/320.1; 435/243; 435/325; 514/11.4; 530/399; 536/23.4

(58) Field of Classification Search
None
See application file for complete search history.

(56) References Cited

U.S. PATENT DOCUMENTS 8,173,782 B2 *  5/2012  Ross et al. .................... 530/399
8,293,709 B2 * 10/2012  Ross et al. .................... 514/11.4

FOREIGN PATENT DOCUMENTS

| WO | WO 01/96565 | 12/2001 |
| WO | WO 2004/090135 | 10/2004 |
| WO | WO 2006/010891 | 2/2006 |
| WO | WO 2007/128979 | 11/2007 |

OTHER PUBLICATIONS

International Search Report and Written Opinion for PCT Application No. PCT/GB2008/002406, 18 pp, (mailed Dec. 10, 2008).
Mode et al., "The Human Growth Hormone (hGH) Antagonist G120RhGH Does Not Antagonize GH in the Rat, But Has Paradoxical Agonist Activity, Probably via the Prolactin Receptor," *Endocrinology*, 137(2): 447-545, (1996).
Pradhananga et al., "Tandem Fusions of Growth Hormone and Its G120R Mutated Antagonist Retain Biological Activity and Demonstrate Prolonged Plasma Half-Life," *Growth Hormone and IGF Research*, 14(2), 1 pp, (Apr. 1, 2004).
Wilkinson et al., "A Ligand-Receptor Fusion of Growth Hormone Forms a Dimer and Is a Potent Long-Acting Agonist," *Nature Medicine*, 13(9): 1108-1113, (Sep. 1, 2007).

* cited by examiner

*Primary Examiner* — Christine J Saoud
(74) *Attorney, Agent, or Firm* — Klarquist Sparkman, LLP

(57) ABSTRACT

We disclose growth hormone [GH] fusion proteins that have increased in vivo stability and activity; nucleic acid molecules encoding said proteins and methods of treatment of growth hormone deficiency that use said fusion proteins. The GH fusion proteins comprise human GH covalently linked to the extracellular domain of Growth Hormone Receptor [GHR] either as a direct in-frame translational fusion or via a flexible peptide linker. The GH/GHR fusion proteins have exceptional pharmacokinetics and are potent growth hormone receptor agonists. The GH/GHR fusion proteins form head to tail dimers.

21 Claims, 10 Drawing Sheets

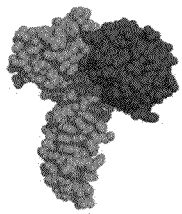
FIG. 1A
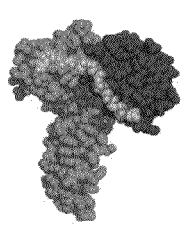
FIG. 1C
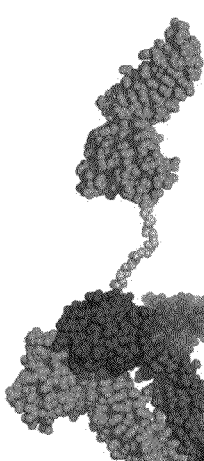
FIG. 1E
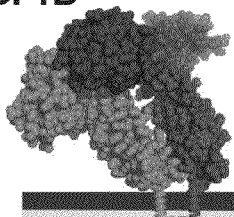
FIG. 1B
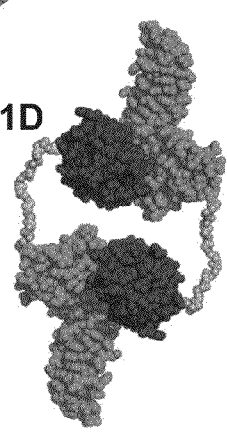
FIG. 1D
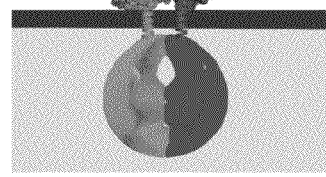

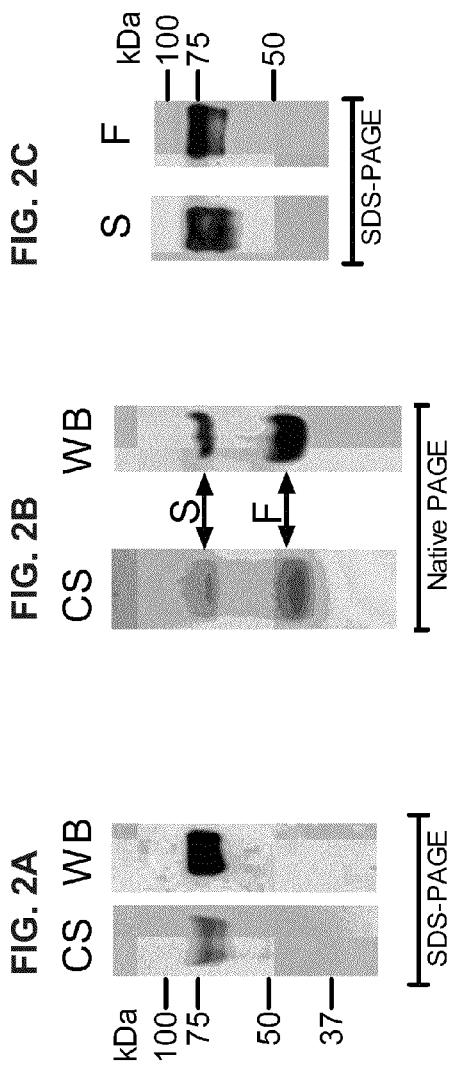
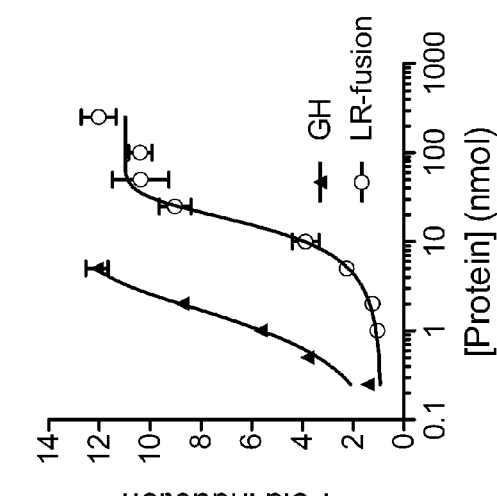
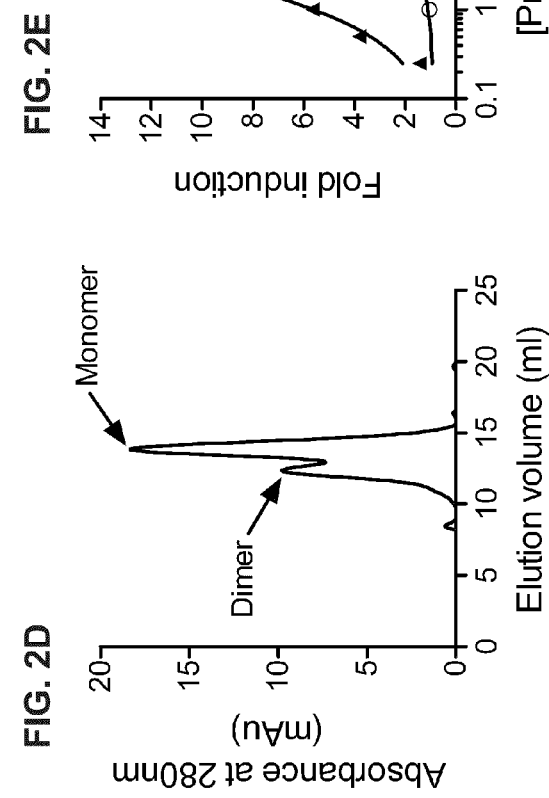
FIG. 2A
FIG. 2B
FIG. 2C
FIG. 2D
FIG. 2E

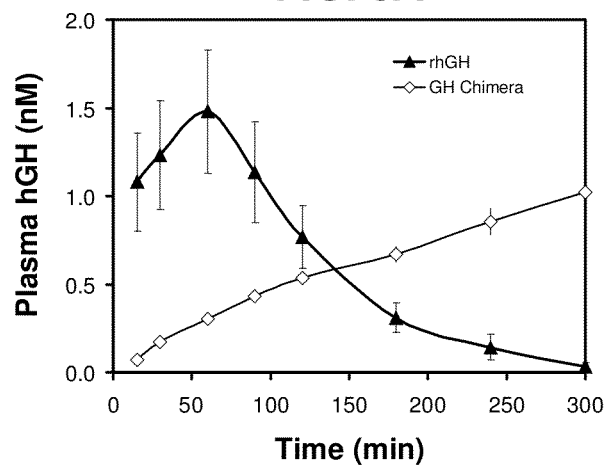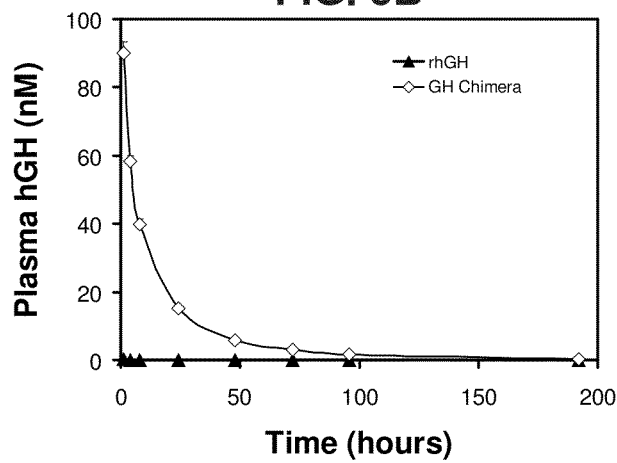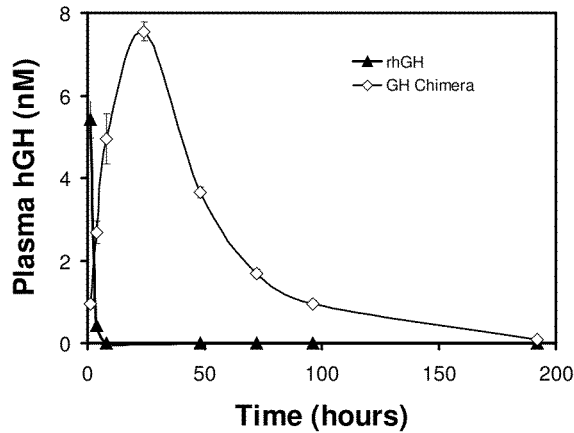

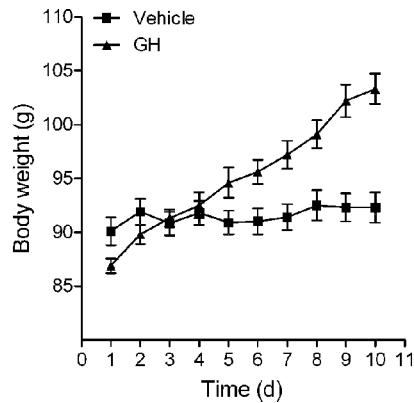
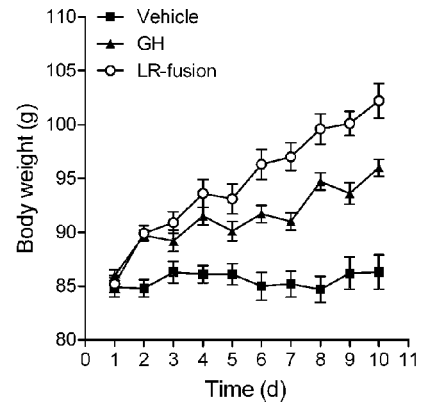
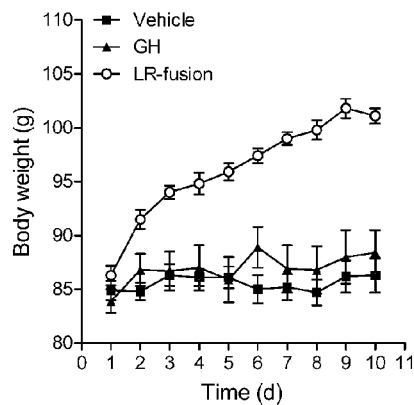
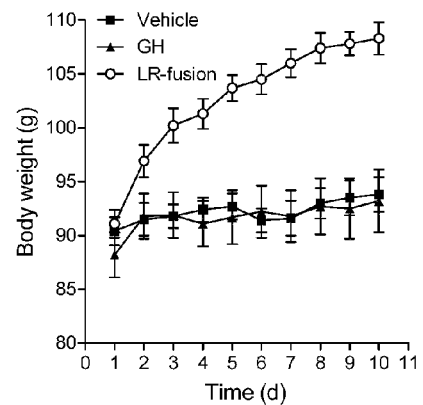
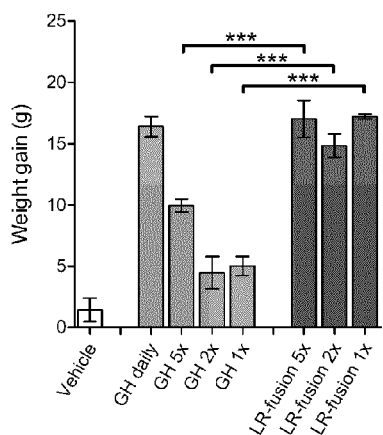

FIG. 6A
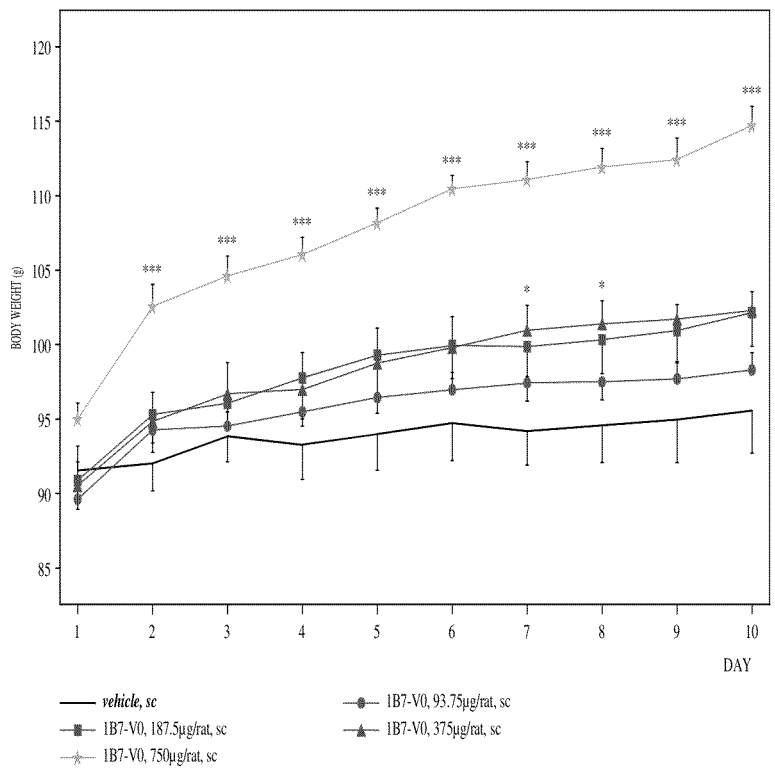
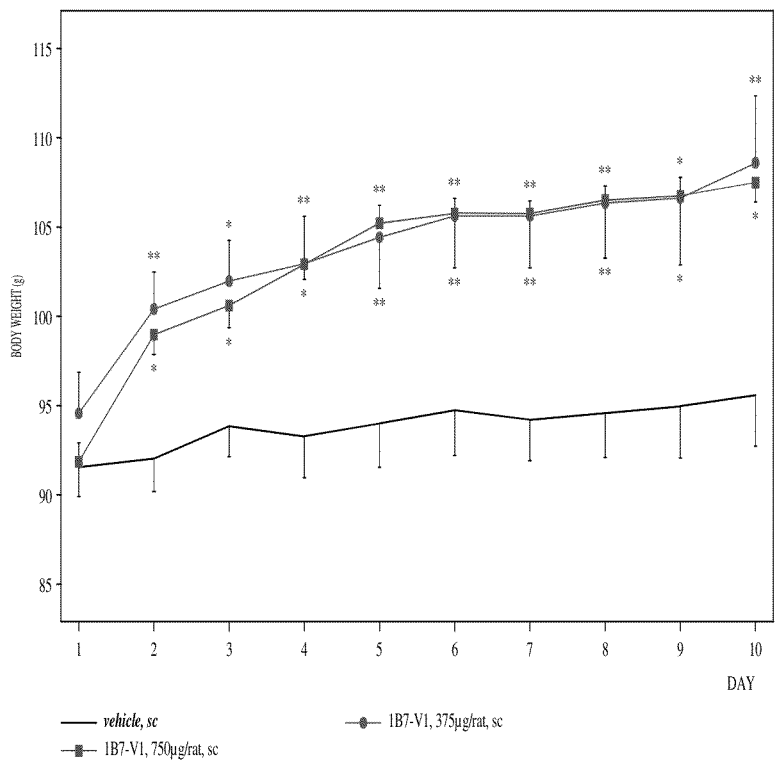

FIG. 6B
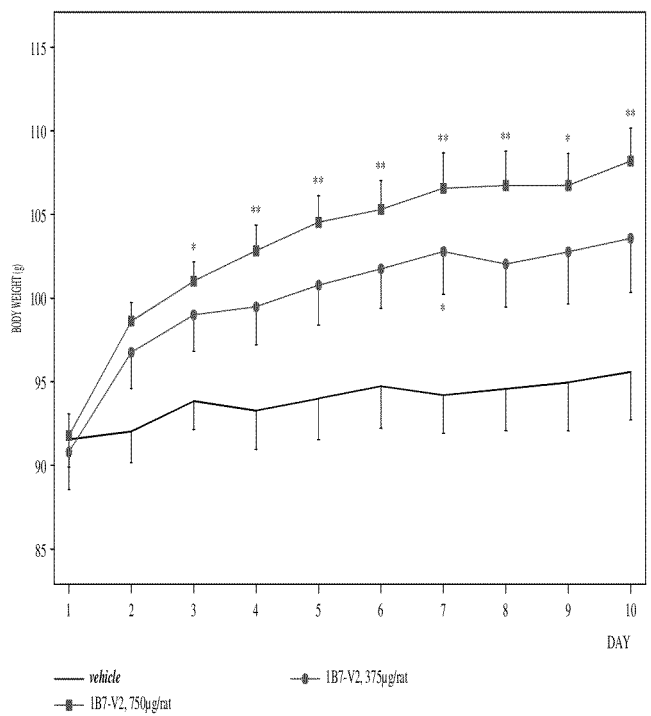
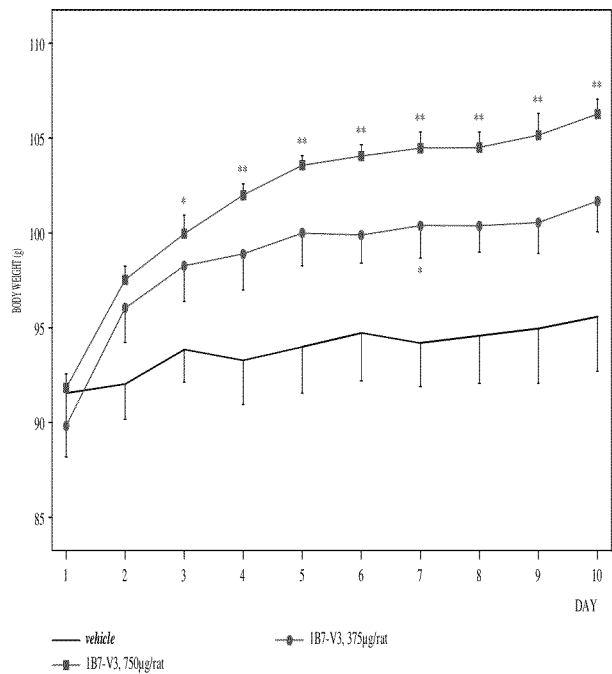

FIG. 7
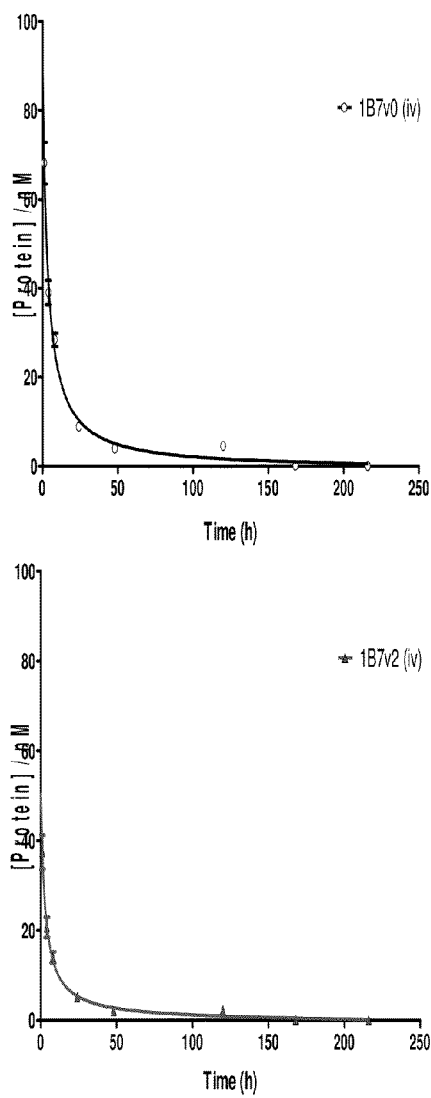
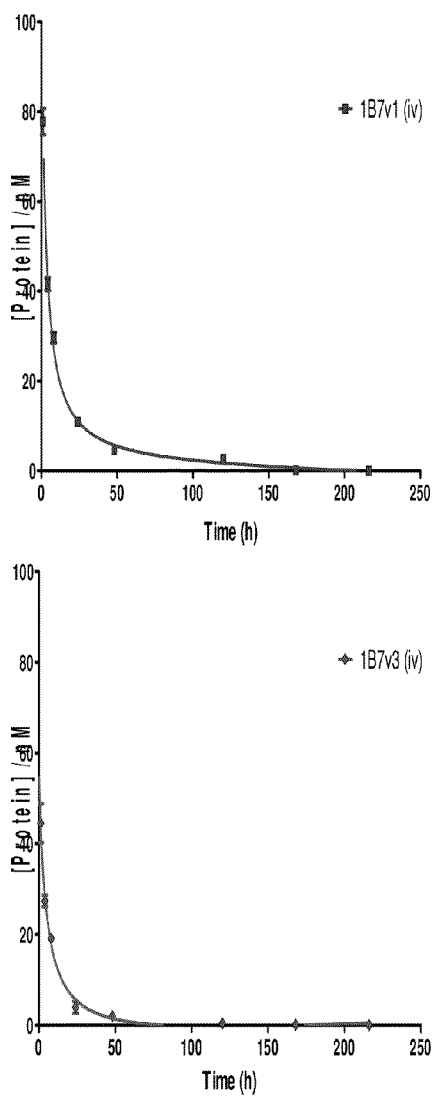

GROWTH HORMONE FUSION PROTEINS

CROSS REFERENCE TO RELATED APPLICATIONS

This is a divisional of U.S. application Ser. No. 12/669,451, filed Jan. 15, 2010, now U.S. Pat. No. 8,293,709, which is incorporated herein by reference, and which is the U.S. national stage of PCT Application No. PCT/GB2008/002406, filed Jul. 16, 2008, which was published in English under PCT Article 21(2). PCT Application No. PCT/GB2008/002406 claims the benefit of U.S. Provisional Application No. 60/951,122, filed Jul. 20, 2007 and claims priority to Great Britain Patent Application No. 0717985.6, filed Sep. 14, 2007.

DETAILED DESCRIPTION

The invention relates to growth hormone fusion proteins; nucleic acid molecules encoding said proteins and methods of treatment that use said proteins.

Ligands that interact with receptors to bring about a biochemical response are known as agonists and those that prevent, or hinder, a biochemical response are known as antagonists. For example, cell specific growth factors are ligands that act as agonists and bind receptors located at the cell surface. Activation of the receptors by ligand-specific binding promotes cell proliferation via activation of intracellular signalling cascades that result in the expression of, amongst other things, cell-cycle specific genes and the activation of quiescent cells to proliferate.

A group of growth factors, referred to as cytokines, are involved in a number of diverse cellular functions. These include modulation of the immune system, regulation of energy metabolism and control of growth and development. Cytokines mediate their effects via receptors expressed at the cell surface on target cells. Cytokine receptors can be divided into three separate sub groups. Type 1 (growth hormone family) receptors are characterised by four conserved cysteine residues in the amino terminal part of their extracellular domain and the presence of a conserved Trp-Ser-Xaa-Trp-Ser motif in the C-terminal part. The repeated Cys motif is also present in Type 2 (interferon family) and Type III (tumour necrosis factor family).

Growth hormone (GH) is an anabolic cytokine hormone important for linear growth in childhood and normal body composition in adults[1]. The current therapeutic regimen for GH replacement requires once-daily subcutaneous injections which is inconvenient and expensive. A number of approaches have been taken to create long-acting preparations, including pegylation[2] and sustained-release formulations[3-5]. Pegylation has the disadvantage that it reduces affinity of hormone for receptor[2], and chemical modification with subsequent purification is expensive. Sustained-release formulations have proven efficacy[4-7] but such GH preparations are characterised by a dominant early-release profile, causing supraphysiological GH levels[3], manufacture is expensive and injections may be painful[4]. There is a need for cytokine formulations that minimise manufacturing costs, have good pharmacokinetic profiles, are easy to administer, and acceptable to patients.

GH acts through a cell-surface type 1 cytokine receptor (GHR). In common with other cytokine receptors, the extracellular domain of the GHR is proteolytically cleaved and circulates as a binding protein (GHBP)[8]. Under physiological conditions GH is in part bound in the circulation in a 1:1 molar ratio by GHBP and this complex appears to be biologically inactive, protected from clearance and degradation[9,10]. A cross-linked complex of GH with GHBP has delayed clearance but no biological activity[11]. Co-administration of separately purified GHBP with GH in a 1:1 ratio can augment the anabolic actions of GH[12]. Thus, like many hormonal systems, binding in the circulation provides an inactive circulating reservoir in equilibrium with active free hormone[13].

Cytokine hormones like growth hormone have a short plasma half-life and require frequent administration. For example, growth hormone (GH) replacement involves daily injections. In common with other cytokines, extracellular domain GH receptor circulates as a binding protein and naturally prolongs GH's biological half-life.

This disclosure relates to the biological actions of a ligand-receptor fusion (LR-fusion) of GH with its extracellular domain receptor. Such a genetically engineered LR-fusion protein was purified from mammalian cell culture. In rats the LR-fusion had a 300-times reduced clearance compared to native GH and single administration promoted growth for 10 days far superior to that seen with native GH. The reduced clearance is reproducible in a primate model. The LR-fusion forms a reciprocal, head-to-tail dimer that provides a reservoir of inactive hormone as occurs naturally with GH and its binding protein.

SEQUENCE LISTING

The Sequence Listing is submitted as an ASCII text file [8617-84284-02_Sequence_Listing.txt, Sep. 11, 2012, 39.7 KB], which is incorporated by reference herein.

According to an aspect of the invention there is provided a nucleic acid molecule comprising a nucleic acid sequence selected from:
  i) a nucleic acid sequence as represented in SEQ ID NO:1;
  ii) a nucleic acid sequence as represented in SEQ ID NO:2;
  iii) a nucleic acid sequence as represented in SEQ ID NO:3;
  iv) a nucleic acid sequence as represented in SEQ ID NO:4; or
  v) a nucleic acid molecule comprising a nucleic sequence that hybridizes under stringent hybridization conditions to SEQ ID NO:1, SEQ ID NO: 2; SEQ ID NO: 3 or SEQ ID NO: 4, and which encodes a polypeptide that has growth hormone receptor agonist activity.

Hybridization of a nucleic acid molecule occurs when two complementary nucleic acid molecules undergo an amount of hydrogen bonding to each other. The stringency of hybridization can vary according to the environmental conditions surrounding the nucleic acids, the nature of the hybridization method, and the composition and length of the nucleic acid molecules used. Calculations regarding hybridization conditions required for attaining particular degrees of stringency are discussed in Sambrook et al., Molecular Cloning: A Laboratory Manual (Cold Spring Harbor Laboratory Press, Cold Spring Harbor, N. Y., 2001); and Tijssen, Laboratory Techniques in Biochemistry and Molecular Biology-Hybridization with Nucleic Acid Probes Part I, Chapter 2 (Elsevier, N.Y., 1993). The $T_m$ is the temperature at which 50% of a given strand of a nucleic acid molecule is hybridized to its complementary strand. The following is an exemplary set of hybridization conditions and is not limiting:

Very High Stringency (Allows Sequences that Share at Least 90% Identity to Hybridize)
  Hybridization: 5×SSC at 65° C. for 16 hours
  Wash twice: 2×SSC at room temperature (RT) for 15 minutes each
  Wash twice: 0.5×SSC at 65° C. for 20 minutes each High Stringency (allows sequences that share at least 80% identity to hybridize)
  Hybridization: 5×-6×SSC at 65° C.-70° C. for 16-20 hours
  Wash twice: 2×SSC at RT for 5-20 minutes each
  Wash twice: 1×SSC at 55° C.-70° C. for 30 minutes each
Low Stringency (Allows Sequences that Share at Least 50% Identity to Hybridize)
  Hybridization: 6×SSC at RT to 55° C. for 16-20 hours
  Wash at least twice: 2×-3×SSC at RT to 55° C. for 20-30 minutes each.

In a preferred embodiment of the invention said nucleic acid molecule comprises or consists of a nucleic acid sequence as represented in SEQ ID NO: 1.

In a preferred embodiment of the invention said nucleic acid molecule comprises or consists of a nucleic acid sequence as represented in SEQ ID NO: 2.

In a preferred embodiment of the invention said nucleic acid molecule comprises or consists of a nucleic acid sequence as represented in SEQ ID NO: 3.

In a preferred embodiment of the invention said nucleic acid molecule comprises or consists of a nucleic acid sequence as represented in SEQ ID NO: 4.

According to an aspect of the invention there is provided a polypeptide encoded by the nucleic acid according to the invention.

According to a further aspect of the invention there is provided a polypeptide comprising an amino acid sequence selected from:
  i) an amino acid sequence as represented in SEQ ID NO:5;
  ii) an amino acid sequence as represented in SEQ ID NO:6;
  iii) an amino acid sequence as represented in SEQ ID NO:7;
  iv) an amino acid sequence as represented in SEQ ID NO:8;
  v) an amino acid sequence as represented in SEQ ID NO:9;
  vi) an amino acid sequence as represented in SEQ ID NO:10;
  vii) an amino acid sequence as represented in SEQ ID NO:11;
  viii) an amino acid sequence as represented in SEQ ID NO:12; wherein said polypeptide has growth hormone receptor agonist activity.

In a preferred embodiment of the invention said polypeptide comprises or consists of an amino acid sequence as represented in SEQ ID NO: 5.

In a preferred embodiment of the invention said polypeptide comprises or consists of an amino acid sequence as represented in SEQ ID NO: 6.

In a preferred embodiment of the invention said polypeptide comprises or consists of an amino acid sequence as represented in SEQ ID NO: 7.

In a preferred embodiment of the invention said polypeptide comprises or consists of an amino acid sequence as represented in SEQ ID NO: 8.

In a preferred embodiment of the invention said polypeptide comprises or consists of an amino acid sequence as represented in SEQ ID NO: 9.

In a preferred embodiment of the invention said polypeptide comprises or consists of an amino acid sequence as represented in SEQ ID NO: 10.

In a preferred embodiment of the invention said polypeptide comprises or consists of an amino acid sequence as represented in SEQ ID NO: 11.

In a preferred embodiment of the invention said polypeptide comprises or consists of an amino acid sequence as represented in SEQ ID NO: 12.

According to a further aspect of the invention there is provided a homodimer comprising two polypeptides comprising or consisting of SEQ ID NO: 5.

According to a further aspect of the invention there is provided a homodimer comprising two polypeptides comprising or consisting of SEQ ID NO: 6.

According to a further aspect of the invention there is provided a homodimer comprising two polypeptides comprising or consisting of SEQ ID NO: 7.

According to a further aspect of the invention there is provided a homodimer comprising two polypeptides comprising or consisting of SEQ ID NO: 8.

According to a further aspect of the invention there is provided a homodimer comprising two polypeptides comprising or consisting of SEQ ID NO: 9.

According to a further aspect of the invention there is provided a homodimer comprising two polypeptides comprising or consisting of SEQ ID NO: 10.

According to a further aspect of the invention there is provided a homodimer comprising two polypeptides comprising or consisting of SEQ ID NO: 11.

According to a further aspect of the invention there is provided a homodimer comprising two polypeptides comprising or consisting of SEQ ID NO: 12.

According to a further aspect of the invention there is provided a vector comprising a nucleic acid molecule according to the invention.

In a preferred embodiment of the invention said vector is an expression vector adapted to express the nucleic acid molecule according to the invention.

A vector including nucleic acid (s) according to the invention need not include a promoter or other regulatory sequence, particularly if the vector is to be used to introduce the nucleic acid into cells for recombination into the genome for stable transfection. Preferably the nucleic acid in the vector is operably linked to an appropriate promoter or other regulatory elements for transcription in a host cell. The vector may be a bi-functional expression vector which functions in multiple hosts. By "promoter" is meant a nucleotide sequence upstream from the transcriptional initiation site and which contains all the regulatory regions required for transcription. Suitable promoters include constitutive, tissue-specific, inducible, developmental or other promoters for expression in eukaryotic or prokaryotic cells. "Operably linked" means joined as part of the same nucleic acid molecule, suitably positioned and oriented for transcription to be initiated from the promoter. DNA operably linked to a promoter is "under transcriptional initiation regulation" of the promoter.

In a preferred embodiment the promoter is a constitutive, an inducible or regulatable promoter.

According to a further aspect of the invention there is provided a cell transfected or transformed with a nucleic acid molecule or vector according to the invention.

Preferably said cell is a eukaryotic cell. Alternatively said cell is a prokaryotic cell.

In a preferred embodiment of the invention said cell is selected from the group consisting of; a fungal cell (e.g. *Pichia* spp, *Saccharomyces* spp, *Neurospora* spp); insect cell (e.g. *Spodoptera* spp); a mammalian cell (e.g. COS cell, CHO cell); a plant cell.

According to a further aspect of the invention there is provided a pharmaceutical composition comprising a polypeptide according to the invention including an excipient or carrier.

In a preferred embodiment of the invention said pharmaceutical composition is combined with a further therapeutic agent.

When administered the pharmaceutical composition of the present invention is administered in pharmaceutically acceptable preparations. Such preparations may routinely contain pharmaceutically acceptable concentrations of salt, buffering agents, preservatives, compatible carriers, and optionally other therapeutic agents.

The pharmaceutical compositions of the invention can be administered by any conventional route, including injection. The administration and application may, for example, be oral, intravenous, intraperitoneal, intramuscular, intracavity, intraarticular, subcutaneous, topical (eyes), dermal (e.g a cream lipid soluble insert into skin or mucus membrane), transdermal, or intranasal.

Pharmaceutical compositions of the invention are administered in effective amounts. An "effective amount" is that amount of pharmaceuticals/compositions that alone, or together with further doses or synergistic drugs, produces the desired response. This may involve only slowing the progression of the disease temporarily, although more preferably, it involves halting the progression of the disease permanently. This can be monitored by routine methods or can be monitored according to diagnostic methods.

The doses of the pharmaceuticals compositions administered to a subject can be chosen in accordance with different parameters, in particular in accordance with the mode of administration used and the state of the subject (i.e. age, sex). When administered, the pharmaceutical compositions of the invention are applied in pharmaceutically-acceptable amounts and in pharmaceutically-acceptable compositions. When used in medicine salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

The pharmaceutical compositions may be combined, if desired, with a pharmaceutically-acceptable carrier. The term "pharmaceutically-acceptable carrier" as used herein means one or more compatible solid or liquid fillers, diluents or encapsulating substances that are suitable for administration into a human. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction that would substantially impair the desired pharmaceutical efficacy.

The pharmaceutical compositions may contain suitable buffering agents, including: acetic acid in a salt; citric acid in a salt; boric acid in a salt; and phosphoric acid in a salt.

The pharmaceutical compositions also may contain, optionally, suitable preservatives, such as: benzalkonium chloride; chlorobutanol; parabens and thimerosal.

The pharmaceutical compositions may conveniently be presented in unit dosage form and may be prepared by any of the methods well-known in the art of pharmacy. All methods include the step of bringing the active agent into association with a carrier that constitutes one or more accessory ingredients. In general, the compositions are prepared by uniformly and intimately bringing the active compound into association with a liquid carrier, a finely divided solid carrier, or both, and then, if necessary, shaping the product.

Compositions suitable for oral administration may be presented as discrete units, such as capsules, tablets, lozenges, each containing a predetermined amount of the active compound. Other compositions include suspensions in aqueous liquids or non-aqueous liquids such as syrup, elixir or an emulsion.

Compositions suitable for parenteral administration conveniently comprise a sterile aqueous or non-aqueous preparation that is preferably isotonic with the blood of the recipient. This preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Carrier formulation suitable for oral, subcutaneous, intravenous, intramuscular, etc. administrations can be found in Remington's Pharmaceutical Sciences, Mack Publishing Co., Easton, Pa.

According to a further aspect of the invention there is provided a method to treat a human subject suffering from growth hormone deficiency comprising administering an effective amount of at least one polypeptide according to the invention.

In a preferred method of the invention said polypeptide is administered intravenously.

In an alternative preferred method of the invention said polypeptide is administered subcutaneously.

In a further preferred method of the invention said polypeptide is administered at two day intervals; preferably said polypeptide is administered at weekly, 2 weekly or monthly intervals.

In a preferred method of the invention said growth hormone deficiency is childhood growth hormone deficiency.

In a preferred method of the invention said growth hormone deficiency is adult growth hormone deficiency.

The treatment of growth hormone deficiency includes for example the treatment of Turners Syndrome, Prader Willi Syndrome, Interuterine growth retardation, idiopathic short stature, renal failure, catabolic states for example during chemotherapy treatment and in the treatment of AIDS.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

An embodiment of the invention will now be described by example only and with reference to the following figures:

FIG. 1 shows a schematic of relationship between GH, GH binding protein (GHBP), LR-fusion and the GHR based on published structures[27] (pdb3HHR): (a) The natural configuration of the GH binding to the GHBP in a 1:1 complex. (b) GH, released from the GHBP complex, binds to the cell surface GH receptor. (c) The LR-fusion molecule in monomeric form with GH linked to exGHR. (d) Model for the LR-fusion forming a reciprocal head-to-tail dimer where GH in one molecule binds to exGHR in the other molecule. Finally in (e) the LR-fusion in monomeric form is capable of binding and activating the GH receptor;

FIG. 2 shows the characterisation and bioactivity of LR-fusion: (a) shows LR-fusion separated by SDS-PAGE followed by Coomassie staining (CS) and western blotting (WB), using a GH specific antibody. The LR-fusion is approximately 75 kDa and separates into two bands approximately 5 kDa apart. (b) shows LR-fusion separated by native PAGE showing that there are two protein forms fast (F) and slow (S). (c) Individual bands (F and S) from the native PAGE were excised and separated further by SDS-PAGE under reducing conditions, followed by western blotting using a GH specific antibody. Both bands (F and S) run at approximately 75 kDa and separate as the doublet previously demonstrated. This suggests that the two distinct bands observed by native PAGE are both composed of the 75 kDa LR-fusion and may exist under native conditions in equilibrium as a monomers and dimers. (d) Shows the elution profile for LR-fusion following gel filtration. The separation of 2 distinct peaks is again indicative of the presence of the LR-fusion as a monomer and dimer in solution. (e) Cell based GHR signalling bioassay for GH and LR-fusion. The y-axis represents the fold induction of corrected luciferase from a Stat 5 luciferase-reporter assay. The standard curve for GH ranges from 0, 0.25, 0.5, 1.0, 2.0 and 5 nM: LR-fusion standard curve ranges from 0, 1, 2, 5, 10, 25, 50, 100 and 250 nM. The maximal response for GH is achieved with 5 nM, whereas the maximal response with the LR-fusion requires 50 to 250 nM;

FIG. 3 shows profiles of GH and LR-fusion measured after subcutaneous (sc) and intravenous (iv) administration: (a) Shows early phase (5 hours) after sc administration; (b) Shows late phase (8 days) after iv; and (c) late phase after sc administration;

FIG. 4 shows the body weight change after subcutaneous treatment with GH and LR-fusion: (a) after daily GH versus placebo (vehicle only); (b) alternate day injections; (c) two injections on days 1 and 5; (d) a single injection day 1; and (e) summary of changes in body weight after different treatment regimens. ***=p<0.0001 GH vs LR-fusion;

FIGS. 6A-6B illustrates a time course showing body weight increase in rats administered 1B7v0 (SEQ ID NO: 5, SEQ ID NO: 6), 1B7v1 (SEQ ID NO: 7, SEQ ID NO: 8), 1B7v2 (SEQ ID NO: 9, SEQ ID NO: 10), and 1B7v3 (SEQ ID NO: 11, SEQ ID NO: 12).

FIG. 7 illustrates the pharmacokinetics of 1B7v0 (SEQ ID NO: 5, SEQ ID NO: 6), 1B7v1 (SEQ ID NO: 7, SEQ ID NO: 8), 1B7v2 (SEQ ID NO: 9, SEQ ID NO: 10), and 1B7v3 (SEQ ID NO: 11, SEQ ID NO: 12) after subcutaneous administration;

Figure 5:
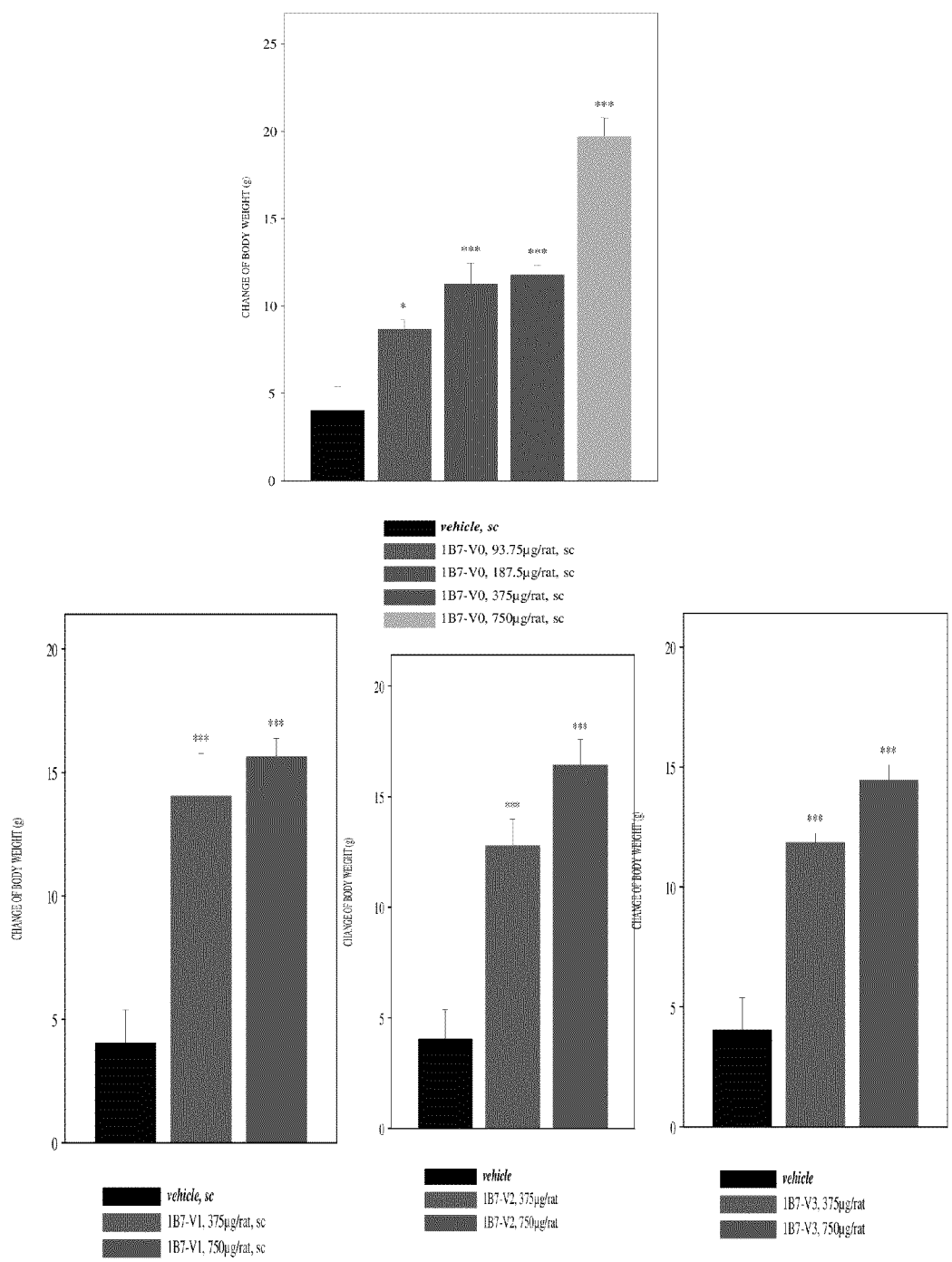
FIG. 5 illustrates the in vivo activity of 1B7v0 (SEQ ID NO: 5, SEQ ID NO: 6), 1B7v1 (SEQ ID NO: 7, SEQ ID NO: 8), 1B7v2 (SEQ ID NO: 9, SEQ ID NO: 10), and 1B7v3 (SEQ ID NO: 11, SEQ ID NO: 12)
Figure 8:
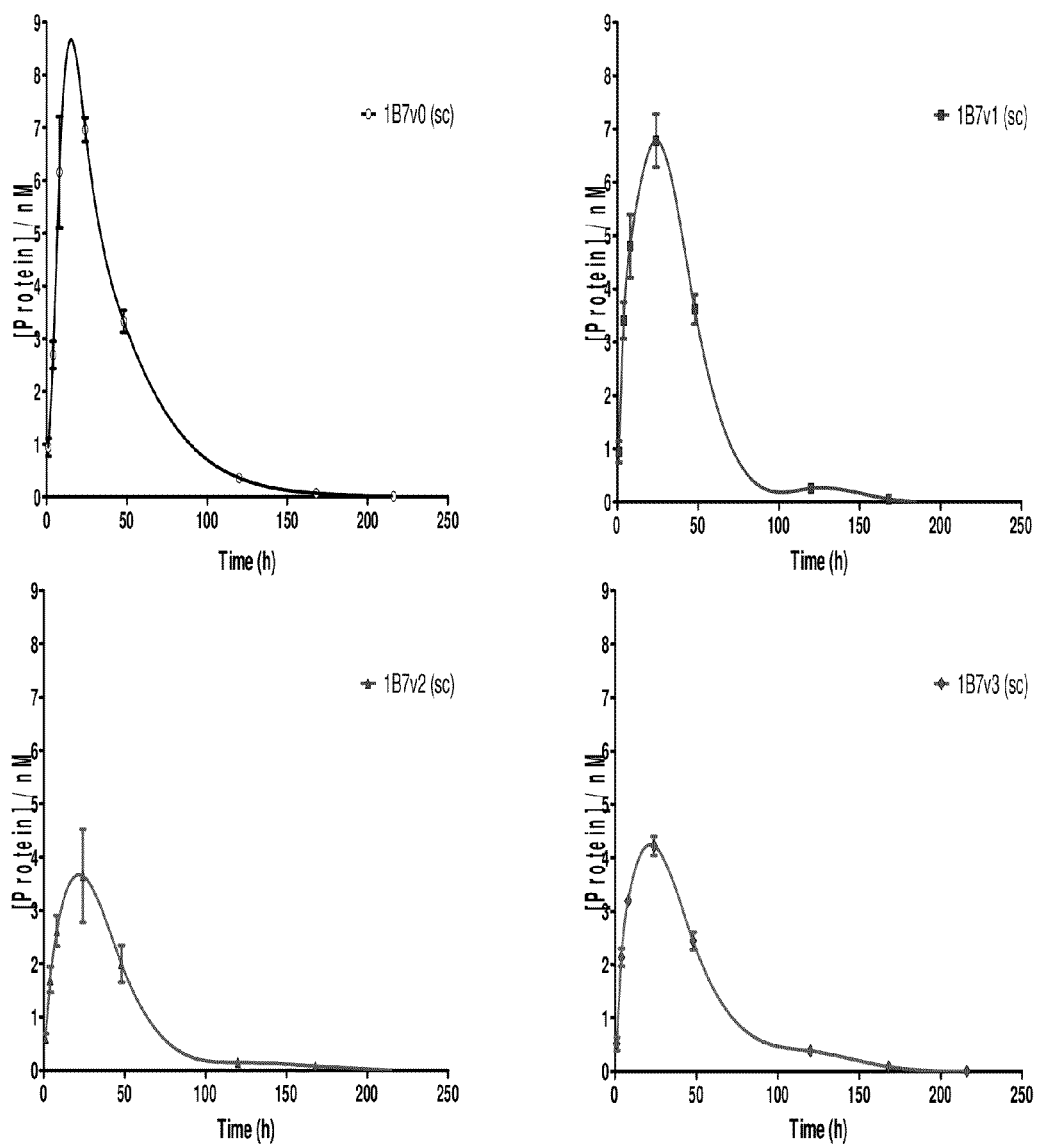
FIG. 8 illustrates the pharmacokinetics of 1B7v0 (SEQ ID NO: 5, SEQ ID NO: 6), 1B7v1 (SEQ ID NO: 7, SEQ ID NO: 8), 1B7v2 (SEQ ID NO: 9, SEQ ID NO: 10), and 1B7v3 (SEQ ID NO: 11, SEQ ID NO: 12) after intravenous administration.

Table 1 shows results (mean±sem) after 10 days treatment with GH or LR-fusion in hypophysectomised rats.

TABLE 1

| Variable at 10 days | Placebo | Treatment | GH | LR-fusion | t-test p GH vs LR |
|---|---|---|---|---|---|
| Weight (g) | 86.3 ± 1.6 | Daily injections | 103.3 ± 1.4 | na | na |
| | | Injections every 2 days | 95.9 ± 0.8 | 102.2 ± 1.6 | <0.0001 |
| | | Injections every 5 days | 88.4 ± 2.1 | 101.1 ± 0.7 | <0.0001 |
| | | Single injection | 93.2 ± 2.9 | 108.3 ± 1.5 | <0.0001 |
| Change in weight from baseline (g) | 1.43 ± 0.96 | Daily injections | 16.4 ± 0.8 | na | na |
| | | Injections every 2 days | 9.9 ± 0.5 | 17 ± 1.5 | 0.0003 |
| | | Injections every 5 days | 4.5 ± 1.3 | 14.8 ± 0.9 | <0.0001 |
| | | Single injection | 5.0 ± 0.1 | 17.2 ± 1.1 | <0.0001 |
| Change in Femur Length (mM) | 0.00 ± 0.25 | Daily injections | 0.83 ± 0.26 | na | na |
| | | Injections every 2 days | 0.99 ± 0.18 | 1.08 ± 0.07 | 0.667 |
| | | Injections every 5 days | 0.44 ± 0.21 | 1.29 ± 0.22 | 0.0194 |
| | | Single injection | na | na | na |
| Change in Tibia weight (g) | 0.00 ± 0.02 | Daily injections | 0.03 ± 0.01 | na | na |
| | | Injections every 2 days | 0.06 ± 0.02 | 0.05 ± 0.01 | 0.52 |
| | | Injections every 5 days | 0.01 ± 0.01 | 0.07 ± 0.02 | 0.027 |
| | | Single injection | na | na | na |

TABLE 1-continued

| Variable at 10 days | Placebo | Treatment | GH | LR-fusion | t-test p GH vs LR |
|---|---|---|---|---|---|
| Change in Thymus weight (mg) | 0.00 ± 21 | Daily injections | 79 ± 20 | na | na |
| | | Injections every 2 days | 43 ± 6 | 142 ± 22 | 0.0054 |
| | | Injections every 5 days | 35 ± 12 | 120 ± 15 | 0.0132 |
| | | Single injection | −13 ± 22 | 117 ± 21 | 0.0017 |
| Change in Liver weight (mg) | 0 ± 167 | Daily injections | 123 ± 170 | na | na |
| | | Injections every 2 days | 362 ± 74 | 587 ± 206 | 0.056 |
| | | Injections every 5 days | 402 ± 236 | 407 ± 116 | 0.073 |
| | | Single injection | na | na | na |
| Change in Kidney weight (mg) | 0 ± 11 | Daily injections | 51 ± 22 | na | na |
| | | Injections every 2 days | 45 ± 26 | 75 ± 21 | 0.0053 |
| | | Injections every 5 days | 5 ± 26 | 67 ± 12 | 0.0273 |
| | | Single injection | 7 ± 22 | 78 ± 15 | 0.0062 |
| IGF-I (ng.ml$^{-1}$) | 51 ± 12 | Daily injections | 92 ± 30 | na | na |
| | | Injections every 2 days | 92 ± 30 | 329 ± 35 | 0.0005 |
| | | Injections every 5 days | 55 ± 15 | 205 ± 5 | <0.0001 |
| | | Single injection | 18 ± 2.5 | 198 ± 66 | 0.0146 |
| GH or Chimera by ELISA (nM) | nd | Daily injections | nd | na | na |
| | | Injections every 2 days | nd | 44 ± 15 | 0.015 |
| | | Injections every 5 days | nd | 23 ± 5 | 0.0015 |
| | | Single injection | nd | 3.2 ± 1.2 | 0.0193 | nd = Not Detectable
na = Not Analyzed

Materials and Methods

Use of Animals and Human Samples.

The use of human samples was approved by the local ethics committee and patients gave informed consent. All the experiments have been conducted in compliance with the French laws (Council Directive N° 86/609/EEC of 24 Nov. 1986) relating to the protection of animals used for experimental or other scientific purpose.

Materials.

All the materials were purchased from Sigma (Poole, UK) unless otherwise stated. Recombinant GH was purchased from Pfizer, recombinant E. coli derived human GH binding protein used in binding assays was a gift from DSL (DSL Research Reagents, Oxfordshire, UK), and iodinated GH a gift from NovoNordisk (NovoNordisk Park, Denmark). GH and GHR mAbs used for purification and characterisation were in-house materials (CS) except mAbs B07b and B24a which were a gift from Dr. Shiver (NovoNordisk Park, Denmark) and mAb 263 (AbD Serotec, Kidlington, Oxford, UK).

Purification of GH-exGHR LR-Fusions.

Human GH and GH receptor were amplified by RT-PCR from human pituitary and liver respectively and cloned into the vector, pSecTag-V5/FRT/Hist-TOPO (Invitrogen, Paisley, UK) under the human GH secretion signal sequence. Four repeats of a Gly$_4$Ser linker were used to link the native C-terminus of human GH to the native N-terminus of the human GHR. Stable clones were made in CHO Flp-In cells (Invitrogen, Paisley, UK), adapted to protein free media and grown in suspension culture. LR-fusion expression was confirmed by an in-house ELISA. Affinity purification was performed using a GH mAb column.

Transcription Bioassays.

These were performed as previously described in human 293 cells stably expressing the human GHR[16].

ELISA. An in house GH and LR-fusion ELISA has been established based on the sandwich ELISA format. In the assay, standards (GH or LR-fusion), controls and unknowns are incubated with biotin-labelled mouse antibody to human GH (mAb 7F8) in wells pre-coated with a mouse antibody to human GH antibody (mAb 10A7). The detection limit for the assay is 2.5 pg and the intra and inter assay CV is <10%. The IGF-I ELISA was purchased from DSL (DSL-10-2900 ACTIVE mouse/rat IGF-I kit; DSL Research Reagents, Oxfordshire, UK).

Pharmacokinetic studies. Seven weeks old normal Sprague Dawley rats from Janvier (Le Genest Saint Isle, France) were used for pharmacokinetic studies. Sc or iv administration (penile vein) and blood withdrawal (orbital sinus) were conducted under isoflurane anaesthesia. The rats (n=4-6/group) were injected iv or sc with of 0.1 mg/kg rhGH or LR-fusion. Blood samples were collected from the retro-orbital plexus. Serum was harvested and stored at −70° C. until assays. Pharmacokinetic parameters were estimated by fitting values of hormone concentration versus time to compartmental models using non-linear least-squares regression analysis. Clearance values were normalized to animal weight. Clearance rate per animal weight and terminal half lives ($t_{1/2}$) were calculated using the coefficient and exponents obtained from the iv bolus model fits.

Primate Pharmacokinetic Study

The test substances IB7v2 (SEQ ID NO: 9, SEQ ID NO: 10) and IB7v3 (SEQ ID NO: 11, SEQ ID NO: 12) were formulated in solutions containing 11.9 mM sodium and potassium phosphates, 137 mM sodium chloride, 2.7 mM potassium chloride, 0.01% polysorbate 80; pH of the solution was adjusted to 7.4.

Study Design

The animals were assigned to 4 treatment groups (1 vehicle, 1 IB7v2 (SEQ ID NO: 9, SEQ ID NO: 10) test group, 1 IB7v3 (SEQ ID NO: 11, SEQ ID NO: 12) test group), comprising 3 males in the vehicle group and 4 males per group in the 2 treatment groups. The dose levels and volumes administered were as outlined in the table below:

| Group | Treatment | # Monkeys (male) | Dose (mg/kg/dose) | Dose Volume |
|---|---|---|---|---|
| 1 | Vehicle (control) | 3 | 0 | 0.2 mL/kg, on days 1, 15 |
| 2 | IB7v2 | 4 | 1 | 0.2 mL/kg, on days 1, 15 |
| 3 | IB7v3 | 4 | 1 | 0.2 mL/kg, on days 1, 15 |

Blood samples were obtained from all animals throughout the study in order to determine the concentration of the appropriate test material in serum. These samples were taken at a number of time points throughout the study.

Clinical Endpoints and Measurements

The serum concentration of IB7v2 (SEQ ID NO: 9, SEQ ID NO: 10) and

IB7v3 (SEQ ID NO: 11, SEQ ID NO: 12) was determined using a validated ELISA method. The pharmacokinetic profile for each of the protein was determined by plotting the concentration for each of the protein in serum versus time using WINNOLIN® Pro (v4.0.1) software.

Growth studies. The growth studies used hypophysectomized rats and were performed on Sprague Dawley rats from Charles River Laboratories (Larbresle, France). Rats were hypophysectomized under isoflurane anaesthesia at 4 weeks of age by the breeder and delivered one week after selection on body weight criteria for successful surgery. Animals were individually caged and allowed another week of rest before entering the experimental phase. The injection solutions of excipient, rhGH and LR-fusion never exceeded 2 ml/kg. The rats were weighed daily and depending on the administration protocol, received injections of the test substances for 10 days.

Characterisation of LR-fusions. Conformation of the LR-fusion was examined using a panel of 16 conformationally sensitive hGH receptor mAbs. Denaturing, native gels and western blotting were used to analyse the LR-fusion and western blotting performed with non-conformationally sensitive to GH. The form of the LR-fusion protein in solution was defined by gel filtration using a Superose G200 analytical column and analytical ultracentrifugation. Analytical ultracentrifugation (AUC) was performed by sedimentation velocity (Analytical service, Dr Andy Barry, Astbury, Leeds University, Leeds, UK).

Statistics.

Two groups were compared with a Student's test if their variance was normally distributed or by a Student-Satterthwaite's test if not normally distributed. Distribution was tested with an F test. One-way ANOVA was used to compare the means of 3 or more groups and if the level of significance was p<0.05 individual comparisons were performed with Dunnett's tests. All statistical tests were two-sided at the 5% level of significance and no imputation was made for missing values.

EXAMPLES

Design and Characterisation of LR-Fusion

A recombinant gene encoding human GH linked to the A & B domains of the GHR extracellular domain (exGHR1-238) via a flexible $(Gly_4Ser)_4$ linker, was generated (FIG. 1c). This LR-fusion was expressed in CHO cells and purified using mAb antibody to GH affinity media to >95% purity (FIG. 2a). The LR-fusion was screened by ELISA using 16 conformationally-sensitive mAbs. All these mAbs bound the LR-fusion with affinity comparable to that for GHBP derived from human serum. Coomassie staining and western blotting of SDS-PAGE gels showed the LR-fusion protein to separate as a doublet of approximately 75 kDa with an approximate 5 kDa difference between the two bands. Native PAGE gel analysis (FIG. 2b) showed no evidence of aggregation. The LR-fusion appeared as two distinct forms. These distinct protein forms, fast (F) and slow (S), were excised from the native PAGE gel and then re-analysed by SDS-PAGE under reducing conditions. Both F & S forms from the native PAGE consisted of the 75 kDa doublet (FIG. 2c). The evidence for the existence of two forms of LR-fusion in solution was confirmed by analytical gel filtration (FIG. 2d). These results are consistent with the LR-fusion existing as a dimer in solution. This was confirmed by analytical ultracentrifugation where the size of the monomer was confirmed at 75 kDa.

In Vitro Bioassay and Pharmacokinetics

The in vitro bioactivity of the LR-fusion was tested using a GH-specific luciferase reporter assay[16]. The LR-fusion had approximately 10% of the bioactivity compared to GH in this static assay system, although the LR-fusion was capable of stimulating maximal response albeit at a higher concentration than GH (FIG. 2e). The LR-fusion's pharmacokinetic profile was examined in normal rats after single subcutaneous (sc) or intravenous (iv) injection (FIG. 3). The LR-fusion demonstrated delayed clearance irrespective of the route of administration and delayed absorption after sc administration. After an iv bolus the terminal half-life of the LR-fusion was 21±2 h, and clearance 3.3±0.9 ml $h^{-1}$ $kg^{-1}$. The clearance of the LR-fusion was 300-times slower than $GH^{2,12}$. After single sc administration the LR-fusion had a delayed peak compared to GH (30 vs 1 hour). The LR-fusion was still detectable at 8 days whilst GH was undetectable at 6 hours. We examined whether the exceptional pharmacokinetics of the LR-fusion were related to size. Two variant LR-fusion molecules with identical linkers were tested: one an LR-fusion of GH to only the B domain exGHR (55 kDa) and the other a tandem (GH linked to GH) linked to exGHR (100 kDa). Both the 55 kDa and 100 kDa proteins showed increased agonist activity in the bioassay compared to the original 75 kDa LR-fusion but for both the circulating half-life was <4 hours after iv administration (precise half-life determination was not possible as the sampling protocol used expected a longer half-life). The results confirm that the exceptional pharmacokinetics of the original 75 kDa LR-fusion was not solely related to molecular weight.

Figure 9:
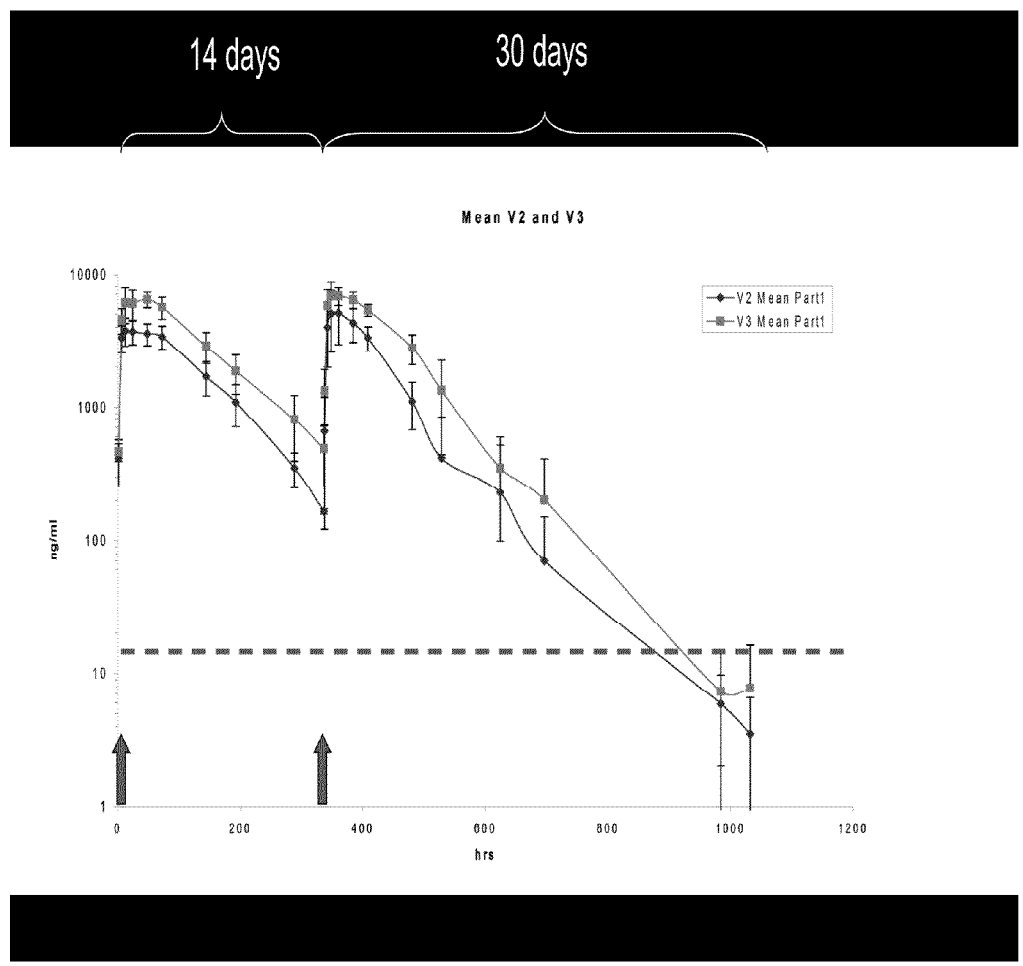
FIG. 9 illustrates pharmacokinetic profiles for IB7v2 (SEQ ID NO: 9, SEQ ID NO: 10) and IB7v3 (SEQ ID NO: 11 and SEQ ID NO: 12) following sequential s/c dosing of 1 mg/kg in rhesus monkey. Red dotted line illustrates the minimum effective concentration for human growth hormone.

The pharmacokinetic profiles in the primate study for IB7v2 and IB7v3 following two sequential s/c doses of 1 mg/kg at t-0 and t-336 hours (14-days) are shown in FIG. 9. It can be noted that the levels reach a maximum rapidly and declines over a significantly extended period of time as compared to native human growth human which has a half-life of <1-hour. The levels are also maintained well above the minimum effective concentration, as defined by the dotted line over the duration of the sequential dosing.

Superiority of LR-Fusion Growth Promotion Over GH

To test biological activity, the LR-fusion and GH were administered to hypophysectomised (GH-deficient) rats. Daily administration of GH induced continuous growth over 10 days. The LR-fusion was then compared to GH with either alternate day sc injections, or two injections over 10 days, or a single injection. For all experiments equimolar doses of GH and LR-fusion were used with the same total dose being given over the 10 day period: 220 µg/kg/day, approximately 10 nmol over 10 days similar to the dose previously used to obtain a maximal growth response[12]. The LR-fusion promoted an increase in weight gain which was greater than GH under the same injection protocol and similar to that seen after daily GH injections (FIG. 4 and Table). GH appeared only to promote weight gain in the 24 hours post injection. In contrast, the LR-fusion produced continuous weight gain over 10 days even when given as a single injection. A similar pattern of growth was seen in femur, tibia, thymus, liver and kidney (Table). The 10-day terminal bleed from all animals was analysed for the GH-dependent biomarker, insulin-like growth factor-I (IGF-I), and GH and LR-fusion levels (Table). IGF-I levels were significantly elevated after LR-fusion administration even after single injection and were significantly greater than those seen after daily injection of GH. Levels of GH were undetectable in the terminal bleed after all injection regimens whereas LR-fusion levels were detectable 10 days after a single injection.

We have demonstrated that an LR-fusion of GH generates a potent agonist. We propose that the ability of the molecule to form a head-to-tail reciprocal dimers (FIG. 1d) is responsible for its enhanced in vivo bioactivity.

The design of the LR-fusion was based on the known crystal structure of the GHR[17]. We used a flexible $Gly_4Ser$ linker with 4 repeats (predicted length of 80 Å). This long linker was chosen as a relatively flexible tether between GH and the GHR such that the GH moiety could still interact with the cell surface GHR (FIG. 1e). Similar $Gly_4Ser$ linkers have been used in recombinant single chain Fv antibody production because of stability and lack of immunogenicity[18].

The LR-fusion was appropriately folded, appearing on both native PAGE gels and in gel filtration as two distinct species, i.e. potentially monomer and dimer. The presence of dimers was confirmed by analytical ultracentrifugation. We propose that the LR-fusion forms a reciprocal head-to-tail dimer through intermolecular binding of the GH moiety in each LR-fusion molecule to the receptor moiety in the other (FIG. 1d). The LR-fusion appeared as two bands on SDS-PAGE, with a molecular weight difference of 5 kDa, presumably due to glycosylation[19,20].

The LR-fusion was more potent in vivo compared to GH but in vitro bioactivity was 10-times less. This discrepancy can be attributed to dimerisation of the LR-fusion. In a static in vitro bioassay the dimer would be biologically inactive as seen with the native GH/GHBP complex[21,22]. However, in vivo the dimer provides a reservoir of inactive hormone in equilibrium with biologically active monomer.

After iv administration to rats our LR-fusion had a 300-times reduced clearance compared to GH and a 10 to 30-times reduced clearance compared to that previously reported for a GH/GHBP complex or conjugate[11,12]. We tested two other LR-fusion variants one of 55 kDa and the other 100 kDa. Neither protein showed the same delayed clearance. We therefore conclude that it is not monomeric size alone that is responsible for LR-fusion delayed clearance. The renal contribution to GH clearance has been estimated to be 25-53% in humans[23] and 67% in rats[24]. Therefore reducing renal clearance alone can only be predicted to approximately halve GH clearance[2]. As GH clearance is relatively independent of a GH receptor mechanism[25] it is presumed that proteolysis is a major contributor. We propose that the greatly reduced clearance of our LR-fusion is attributable to both reduced renal clearance and a conformation that prevents proteolysis.

In hypophysectomised rats our LR-fusion given only once during 10 days produced a similar increase in weight to that seen with daily injections of GH. It has previously been shown that GHBP co-administered as 1:1 molar complex with GH augments growth[12]. Using the same protocol our LR-fusion protein promoted growth over 10 days after a single injection whereas the GH/GHBP complex required daily injections and our LR-fusion generated a higher IGF-I level than that seen after GH/GHBP co-administration. GH is biologically inactive when conjugated to GHBP and the non-covalently linked complex lacks the stability of the LR-fusion[11,12]. The greater biological action of the LR-fusion may relate to its increased stability and its ability to activate the GHR in monomeric form.

In humans IGF-I levels are generally a good biomarker of GH activity. However, in hypophysectomised rats IGF-I levels do not always reflect the growth response to GH[2,12]. LR-fusion administration resulted in clearly elevated IGF-I levels compared to GH injection. We suggest that the dose-response to GH of growth and IGF-I differs in hypophysectomised rats. Thus, the dose of LR-fusion used in our study was in excess of that required to promote a maximal growth response, but still capable of stimulating IGF-I generation. Rats display more rapid renal clearance than humans making it difficult to predict the dosing regimen that will be required in man. One might expect that the LR-fusion could be used at lower doses and much less frequently than GH.

Fusions of cytokine hormones with serum albumin and pegylation have been used to prolong circulating half-life[2,26]. Our LR-fusion molecule has major advantages over these two approaches. Pegylation is highly effective at delaying the clearance of proteins, but requires chemical modification and reduces the affinity of ligand for its receptor[2]. Thus, with pegylation a greater dose is required whereas with our LR-fusion a similar dose has a greater effect than native GH. Regarding the GH fusion with albumen, Albutropin, relatively little is known as it is understood that this was withdrawn from clinical studies. In the one PK study Albutropin had 6-times longer terminal half-life when given s.c.compared to GH whereas our LR-fusion protein has a 100-times longer terminal half-life given i.v. compared to that published for GH[12] (For native human GH: clearance value of 18.6 ml/min.kg=1116 ml/hr.kg and Vd=336 ml/kg thus T1/2=0.693×336/1116=0.21 hrs.). GH naturally binds to circulating exGHR and therefore our LR-fusion is unlikely to be immunogenic compared to fusions with other proteins and extensive in silico T cell epitope screening showed no sites in the LR-fusion molecule (data not shown).

REFERENCES

1. Woodhouse, L. J., Mukherjee, A., Shalet, S. M. & Ezzat, S. The influence of growth hormone status on physical impairments, functional limitations, and health-related quality of life in adults. Endocr Rev. 27, 287-317 (2006).
2. Clark, R. et al. Long-acting growth hormones produced by conjugation with polyethylene glycol. Journal of Biological Chemistry. 271, 21969-21977 (1996).
3. Cook, D. M. et al. The pharmacokinetic and pharmacodynamic characteristics of a long-acting growth hormone (GH) preparation (nutropin depot) in GH-deficient adults. J Clin Endocrinol Metab. 87, 4508-14 (2002).

4. Reiter, E. O. et al. A multicenter study of the efficacy and safety of sustained release GH in the treatment of naive pediatric patients with GH deficiency. J Clin Endocrinol Metab. 86, 4700-6 (2001).
5. Jostel, A., Mukherjee, A., Alenfall, J., Smethurst, L. & Shalet, S. M. A new sustained-release preparation of human growth hormone and its pharmacokinetic, pharmacodynamic and safety profile. Clin Endocrinol (Oxf). 62, 623-7 (2005).
6. Laursen, T. et al. Long-term effects of continuous subcutaneous infusion versus daily subcutaneous injections of growth hormone (GH) on the insulin-like growth factor system, insulin sensitivity, body composition, and bone and lipoprotein metabolism in GH-deficient adults. J Clin Endocrinol Metab. 86, 1222-8 (2001).
7. Laursen, T., Jorgensen, J. O., Jakobsen, G., Hansen, B. L. & Christiansen, J. S. Continuous infusion versus daily injections of growth hormone (GH) for 4 weeks in GH-deficient patients. J Clin Endocrinol Metab. 80, 2410-8 (1995).
8. Muller-Newen, G., Kohne, C. & Heinrich, P. C. Soluble receptors for cytokines and growth factors. [Review][58 refs]. International Archives of Allergy & Immunology. 111, 99-106 (1996).
9. Baumann, G., Amburn, K. D. & Buchanan, T. A. The effect of circulating growth hormone-binding protein on metabolic clearance, distribution, and degradation of human growth hormone. J Clin Endocrinol Metab. 64, 657-60 (1987).
10. Baumann, G. Growth hormone heterogeneity: genes, isohormones, variants, and binding proteins. Endocrine Reviews 12, 424-449 (1991).
11. Baumann, G., Shaw, M. A. & Buchanan, T. A. In vivo kinetics of a covalent growth hormone-binding protein complex. Metabolism. 38, 330-3 (1989).
12. Clark, R. G. et al. Recombinant human growth hormone (GH)-binding protein enhances the growth-promoting activity of human GH in the rat. Endocrinology. 137, 4308-4315 (1996).
13. Baumann, G. Growth hormone binding protein—errant receptor or active player? [editorial]. Endocrinology. 136, 377-378 (1995).
14. Ayling, R. M. et al. A dominant-negative mutation of the growth hormone receptor causes familial short stature. Nature Genetics. 16, 13-14 (1997).
15. Ross, R. J. et al. A short isoform of the human growth hormone receptor functions as a dominant negative inhibitor of the full-length receptor and generates large amounts of binding protein. Molecular Endocrinology. 11, 265-273 (1997).
16. Ross, R. J. M. et al. Binding and functional studies with the growth hormone receptor antagonist, B2036-PEG (pegvisomant), reveal effects of pegylation and evidence that it binds to a receptor dimer. Journal of Clinical Endocrinology & Metabolism. 86, 1716-1723 (2001).
17. Cunningham, B. C. et al. Dimerization of the extracellular domain of the human growth hormone receptor by a single hormone molecule. Science. 254, 821-825 (1991).
18. Huston, J. S., Tai, M. S., McCartney, J., Keck, P. & Oppermann, H. Antigen recognition and targeted delivery by the single-chain Fv. Cell Biophys. 22, 189-224 (1993).
19. Herington, A. C., Smith, A. I., Wallace, C. & Stevenson, J. L. Partial purification from human serum of a specific binding protein for human growth hormone. Mol Cell Endocrinol. 53, 203-9 (1987).
20. Frick, G. P., Tai, L. R., Baumbach, W. R. & Goodman, H. M. Tissue distribution, turnover, and glycosylation of the long and short growth hormone receptor isoforms in rat tissues. Endocrinology. 139, 2824-30 (1998).
21. Mannor, D. A., Winer, L. M., Shaw, M. A. & Baumann, G. Plasma growth hormone (GH)-binding proteins: effect on GH binding to receptors and GH action. J Clin Endocrinol Metab. 73, 30-4 (1991).
22. Lim, L., Spencer, S. A., McKay, P. & Waters, M. J. Regulation of growth hormone (GH) bioactivity by a recombinant human GH-binding protein. Endocrinology. 127, 1287-91 (1990).
23. Haffner, D., Schaefer, F., Girard, J., Ritz, E. & Mehls, O. Metabolic clearance of recombinant human growth hormone in health and chronic renal failure. J Clin Invest. 93, 1163-71 (1994).
24. Johnson, V. & Maack, T. Renal extraction, filtration, absorption, and catabolism of growth hormone. American Journal of Physiology 233, F185-F196 (1977).
25. Veldhuis, J. D. et al. Impact of experimental blockade of peripheral growth hormone (GH) receptors on the kinetics of endogenous and exogenous GH removal in healthy women and men. Journal of Clinical Endocrinology & Metabolism 87, 5737-5745 (2002).
26. Osborn, B. L. et al. Albutropin: a growth hormone-albumin fusion with improved pharmacokinetics and pharmacodynamics in rats and monkeys. Eur J Pharmacol 456, 149-58 (2002).
27. de Vos, A. M., Ultsch, M. & Kossiakoff, A. A. Human growth hormone and extracellular domain of its receptor: crystal structure of the complex. Science 255, 306-312 (1992)

The invention claimed is:

1. A nucleic acid molecule comprising a nucleic acid sequence as set forth as SEQ ID NO: 3 which encodes a polypeptide that has growth hormone receptor agonist activity.

2. A polypeptide comprising an amino acid sequence selected from the group consisting of:
   i) the amino acid sequence as set forth as SEQ ID NO:9; and
   ii) the amino acid sequence as set forth as SEQ ID NO:10;
   wherein said polypeptide has growth hormone receptor agonist activity.

3. The polypeptide according to claim 2 wherein said polypeptide comprises an amino acid sequence as set forth as SEQ ID NO: 9.

4. A homodimer comprising two polypeptides according to claim 3, each of the two polypeptides comprising the amino acid sequence as set forth as SEQ ID NO: 9.

5. The polypeptide according to claim 2 wherein said polypeptide comprises an amino acid sequence as set forth as SEQ ID NO: 10.

6. A homodimer comprising two polypeptides according to claim 5, each of the two polypeptides comprising the amino acid sequence as set forth as SEQ ID NO: 10.

7. A pharmaceutical composition comprising a polypeptide according to claim 2 including an excipient or carrier.

8. A method to treat a human subject suffering from growth hormone deficiency comprising administering an effective amount of at least one polypeptide according to claim 2, thereby treating the subject suffering from the growth hormone deficiency.

9. The method according to claim 8 wherein said polypeptide is administered intravenously.

10. The method according to claim 8 wherein said polypeptide is administered subcutaneously.

11. The method according to claim 8 wherein said polypeptide is administered at two day intervals.

12. The method according to claim 8 wherein said polypeptide is administered at weekly intervals.

13. The method according to claim 8 wherein said polypeptide is administered at 2 weekly intervals.

14. The method according to claim 8 wherein said polypeptide is administered at monthly intervals.

15. The method according to claim 8 wherein said growth hormone deficiency is childhood growth hormone deficiency.

16. The method according to claim 8 wherein said growth hormone deficiency is adult growth hormone deficiency.

17. A vector comprising a nucleic acid molecule according to claim 1.

18. The vector according to claim 17 wherein said vector is an expression vector.

19. An isolated cell transfected or transformed with a vector according to claim 18.

20. The cell according to claim 19 wherein said cell is a eukaryotic cell.

21. The cell according to claim 19 wherein said cell is a prokaryotic cell.

* * * * *

SEQUENCE LISTING

<160> NUMBER OF SEQ ID NOS: 12

<210> SEQ ID NO 1
<211> LENGTH: 1455
<212> TYPE: DNA
<213> ORGANISM: Artificial
<220> FEATURE:
<223> OTHER INFORMATION: growth hormone/receptor fusion protein

<400> SEQUENCE: 1

```
atggctacag gtccccggac gtccctgctc ctggcttttg gcctgctctg cctgccctgg      60
cttcaagagg gcagtgcctt cccaaccatt cccttatcca ggcttttga caacgctatg     120
```

```
ctccgcgccc atcgtctgca ccagctggcc tttgacacct accaggagtt tgaagaagcc    180
tatatcccaa aggaacagaa gtattcattc ctgcagaacc cccagacctc cctctgtttc    240
tcagagtcta ttccgacacc ctccaacagg aggaaacac aacagaaatc caacctagag    300
ctgctccgca tctccctgct gctcatccag tcgtggctgg agcccgtgca gttcctcagg    360
agtgtcttcg ccaacagcct ggtgtacggc gcctctgaca gcaacgtcta tgacctccta    420
aaggacctag aggaaggcat ccaaacgctg atggggaggc tggaagatgg cagccccgg    480 actgggcaga tcttcaagca gacctacagc aagttcgaca caaactcaca caacgatgac    540
gcactactca agaactacgg gctgctctac tgcttcagga aggacatgga caaggtcgag    600
acattcctgc gcatcgtgca gtgccgctct gtggagggca gctgtggctt cggcggccgc    660
ggtggcggag gtagtggtgg cggaggtagc ggtggcggag gttctggtgg cggaggttcc    720
gaattctttt ctggaagtga ggccacagca gctatcctta gcagagcacc ctggagtctg    780
caaagtgtta atccaggcct aaagacaaat tcttctaagg agcctaaatt caccaagtgc    840
cgttcacctg agcgagagac ttttttcatgc cactggacag atgaggttca tcatggtaca    900
aagaacctag acccataca gctgttctat accagaagga acactcaaga atggactcaa    960
gaatggaaag aatgccctga ttatgttttct gctggggaaa acagctgtta ctttaattca    1020
tcgtttacct ccatctggat accttattgt atcaagctaa ctagcaatgg tggtacagtg    1080
gatgaaaagt gtttctctgt tgatgaaata gtgcaaccag atccacccat tgccctcaac    1140
tggactttac tgaacgtcag tttaactggg attcatgcag atatccaagt gagatgggaa    1200
gcaccacgca atgcagatat tcagaaagga tggatggttc tggagtatga acttcaatac    1260
aaagaagtaa atgaaactaa atggaaaatg atggaccccta tattgacaac atcagttcca    1320
gtgtactcat tgaaagtgga taaggaatat gaagtacgcg tgagatccaa acaacgaaac    1380
tctggaaatt atggcgagtt cagtgaggtg ctctatgtaa cacttcctca gatgagccaa    1440
aagcttttcg aataa                                                    1455

<210> SEQ ID NO 2
<211> LENGTH: 1443
<212> TYPE: DNA
<213> ORGANISM: Artificial
<220> FEATURE:
<223> OTHER INFORMATION: growth hormone/receptor fusion

<400> SEQUENCE: 2
atggctacag gctcccggac gtccctgctc ctggcttttg gcctgctctg cctgcctgg    60 cttcaagagg gcagtgcctt cccaaccatt cccttatcca ggcttttga caacgctatg    120 ctccgcgccc atcgtctgca ccagctggcc tttgacacct accaggagtt tgaagaagcc    180
tatatcccaa aggaacagaa gtattcattc ctgcagaacc cccagacctc cctctgtttc    240
tcagagtcta ttccgacacc ctccaacagg aggaaacac aacagaaatc caacctagag    300
ctgctccgca tctccctgct gctcatccag tcgtggctgg agcccgtgca gttcctcagg    360
agtgtcttcg ccaacagcct ggtgtacggc gcctctgaca gcaacgtcta tgacctccta    420
aaggacctag aggaaggcat ccaaacgctg atggggaggc tggaagatgg cagccccgg    480 actgggcaga tcttcaagca gacctacagc aagttcgaca caaactcaca caacgatgac    540
gcactactca agaactacgg gctgctctac tgcttcagga aggacatgga caaggtcgag    600
acattcctgc gcatcgtgca gtgccgctct gtggagggca gctgtggctt cggcggccgc    660
ggtggcggag gtagtggtgg cggaggtagc ggtggcggag gttctggtgg cggaggttcc    720
```

```
gaattcttttt ctggaagtga ggccacagca gctatcctta gcagagcacc ctggagtctg      780
caaagtgtta atccaggcct aaagacaaat tcttctaagg agcctaaatt caccaagtgc      840
cgttcacctg agcgagagac tttttcatgc cactggacag atgaggttca tcatggtaca      900
aagaacctag acccataca gctgttctat accagaagga acactcaaga atggactcaa      960
gaatggaaag aatgccctga ttatgtttct gctggggaaa acagctgtta ctttaattca     1020
tcgtttacct ccatctggat accttattgt atcaagctaa ctagcaatgg tggtacagtg     1080
gatgaaaagt gtttctctgt tgatgaaata gtgcaaccag atccacccat tgccctcaac     1140
tggactttac tgaacgtcag tttaactggg attcatgcag atatccaagt gagatgggaa     1200
gcaccacgca atgcagatat tcagaaagga tggatggttc tggagtatga acttcaatac     1260
aaagaagtaa atgaaactaa atggaaaatg atggaccata tattgacaac atcagttcca     1320
gtgtactcat tgaaagtgga taaggaatat gaagtgcgtg tgagatccaa acaacgaaac     1380
tctggaaatt atggcgagtt cagtgaggtg ctctatgtaa cacttcctca gatgagccaa     1440
taa                                                                    1443
```

```
<210> SEQ ID NO 3
<211> LENGTH: 1443
<212> TYPE: DNA
<213> ORGANISM: Artificial
<220> FEATURE:
<223> OTHER INFORMATION: growth hormone/receptor fusion

<400> SEQUENCE: 3
```

```
atggctacag gctcccggac gtccctgctc ctggcttttg gcctgctctg cctgccctgg        60
cttcaagagg gcagtgcctt cccaaccatt cccttatcca ggcttttgta caacgctatg       120
ctccgcgccc atcgtctgca ccagctggcc tttgacacct accaggagtt tgaagaagcc       180
tatatcccaa aggaacagaa gtattcattc ctgcagaacc cccagacctc cctctgtttc       240
tcagagtcta ttccgacacc ctccaacagg gaggaaacac aacagaaatc caacctagag       300
ctgctccgca tctccctgct gctcatccag tcgtggctgg agcccgtgca gttcctcagg       360
agtgtcttcg ccaacagcct ggtgtacggc gcctctgaca gcaacgtcta tgacctccta       420
aaggacctag aggaaggcat ccaaacgctg atggggaggc tggaagatgg cagccccggg       480
actgggcaga tcttcaagca gacctacagc aagttcgaca caaactcaca caacgatgac       540
gcactactca gaactacggg ctgctctac tgcttcagga aggacatgga caaggtcgag       600
acattcctgc gcatcgtgca gtgccgctct gtggagggca gctgtggctt cggtggcgga       660
ggtagtggtg gcggaggtag cggtggcgga ggttctggtg gcggaggttc cggtggcgga       720
ggtagttttt ctggaagtga ggccacagca gctatcctta gcagagcacc ctggagtctg       780
caaagtgtta atccaggcct aaagacaaat tcttctaagg agcctaaatt caccaagtgc       840
cgttcacctg agcgagagac tttttcatgc cactggacag atgaggttca tcatggtaca       900
aagaacctag acccataca gctgttctat accagaagga acactcaaga atggactcaa       960
gaatggaaag aatgccctga ttatgtttct gctggggaaa acagctgtta ctttaattca      1020
tcgtttacct ccatctggat accttattgt atcaagctaa ctagcaatgg tggtacagtg      1080
gatgaaaagt gtttctctgt tgatgaaata gtgcaaccag atccacccat tgccctcaac      1140
tggactttac tgaacgtcag tttaactggg attcatgcag atatccaagt gagatgggaa      1200
gcaccacgca atgcagatat tcagaaagga tggatggttc tggagtatga acttcaatac      1260
aaagaagtaa atgaaactaa atggaaaatg atggaccata tattgacaac atcagttcca      1320
```

-continued

| | |
|---|---|
| gtgtactcat tgaaagtgga taaggaatat gaagtgcgtg tgagatccaa acaacgaaac | 1380 |
| tctggaaatt atggcgagtt cagtgaggtg ctctatgtaa cacttcctca gatgagccaa | 1440 |
| taa | 1443 |

<210> SEQ ID NO 4
<211> LENGTH: 1368
<212> TYPE: DNA
<213> ORGANISM: Artificial
<220> FEATURE:
<223> OTHER INFORMATION: growth hormone/receptor fusion

<400> SEQUENCE: 4

| | |
|---|---|
| atggctacag gctcccggac gtccctgctc ctggcttttg gcctgctctg cctgccctgg | 60 |
| cttcaagagg gcagtgcctt cccaaccatt cccttatcca ggcttttga caacgctatg | 120 |
| ctccgcgccc atcgtctgca ccagctggcc tttgacacct accaggagtt tgaagaagcc | 180 |
| tatatcccaa aggaacagaa gtattcattc ctgcagaacc cccagacctc cctctgtttc | 240 |
| tcagagtcta ttccgacacc ctccaacagg aggaaacac aacagaaatc caacctagag | 300 |
| ctgctccgca tctccctgct gctcatccag tcgtggctgg agcccgtgca gttcctcagg | 360 |
| agtgtcttcg ccaacagcct ggtgtacggc gcctctgaca gcaacgtcta tgacctccta | 420 |
| aaggacctag aggaaggcat ccaaacgctg atggggaggc tggaagatgg cagccccgg | 480 |
| actgggcaga tcttcaagca gacctacagc aagttcgaca caaactcaca caacgatgac | 540 |
| gcactactca gaactacgg gctgctctac tgcttcagga aggacatgga caaggtcgag | 600 |
| acattcctgc gcatcgtgca gtgccgctct gtggagggca gctgtggctt cttttctgga | 660 |
| agtgaggcca cagcagctat ccttagcaga gcaccctgga gtctgcaaag tgttaatcca | 720 |
| ggcctaaaga caaattcttc taaggagcct aaattcacca agtgccgttc acctgagcga | 780 |
| gagactttt catgccactg gacagatgag gttcatcatg gtacaaagaa cctaggaccc | 840 |
| atacagctgt tctataccag aaggaacact caagaatgga ctcaagaatg aaagaatgc | 900 |
| cctgattatg tttctgctgg ggaaaacagc tgttacttta attcatcgtt acctccatc | 960 |
| tggatacctt attgtatcaa gctaactagc aatggtggta cagtggatga aaagtgtttc | 1020 |
| tctgttgatg aaatagtgca accagatcca cccattgccc tcaactggac tttactgaac | 1080 |
| gtcagtttaa ctgggattca tgcagatatc caagtgagat gggaagcacc acgcaatgca | 1140 |
| gatattcaga aggatggat ggttctggag tatgaacttc aatacaaaga agtaaatgaa | 1200 |
| actaaatgga aaatgatgga ccctatattg acaacatcag ttccagtgta ctcattgaaa | 1260 |
| gtggataagg aatatgaagt gcgtgtgaga tccaaacaac gaaactctgg aaattatggc | 1320 |
| gagttcagtg aggtgctcta tgtaacactt cctcagatga gccaataa | 1368 |

<210> SEQ ID NO 5
<211> LENGTH: 484
<212> TYPE: PRT
<213> ORGANISM: Artificial
<220> FEATURE:
<223> OTHER INFORMATION: growth hormone/receptor fusion

<400> SEQUENCE: 5

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala His Arg Leu His Gln
        35                  40                  45

```
Leu Ala Phe Asp Thr Tyr Gln Glu Phe Glu Ala Tyr Ile Pro Lys
    50                  55                  60
Glu Gln Lys Tyr Ser Phe Leu Gln Asn Pro Gln Thr Ser Leu Cys Phe
65                  70                  75                  80
Ser Glu Ser Ile Pro Thr Pro Ser Asn Arg Glu Glu Thr Gln Gln Lys
                85                  90                  95
Ser Asn Leu Glu Leu Leu Arg Ile Ser Leu Leu Leu Ile Gln Ser Trp
                100                 105                 110
Leu Glu Pro Val Gln Phe Leu Arg Ser Val Phe Ala Asn Ser Leu Val
            115                 120                 125
Tyr Gly Ala Ser Asp Ser Asn Val Tyr Asp Leu Leu Lys Asp Leu Glu
    130                 135                 140
Glu Gly Ile Gln Thr Leu Met Gly Arg Leu Glu Asp Gly Ser Pro Arg
145                 150                 155                 160
Thr Gly Gln Ile Phe Lys Gln Thr Tyr Ser Lys Phe Asp Thr Asn Ser
                165                 170                 175
His Asn Asp Asp Ala Leu Leu Lys Asn Tyr Gly Leu Leu Tyr Cys Phe
                180                 185                 190
Arg Lys Asp Met Asp Lys Val Glu Thr Phe Leu Arg Ile Val Gln Cys
            195                 200                 205
Arg Ser Val Glu Gly Ser Cys Gly Phe Gly Arg Gly Gly Gly
    210                 215                 220
Ser Gly Gly Gly Ser Gly Gly Gly Ser Gly Gly Gly Ser
225                 230                 235                 240
Glu Phe Phe Ser Gly Ser Glu Ala Thr Ala Ala Ile Leu Ser Arg Ala
                245                 250                 255
Pro Trp Ser Leu Gln Ser Val Asn Pro Gly Leu Lys Thr Asn Ser Ser
            260                 265                 270
Lys Glu Pro Lys Phe Thr Lys Cys Arg Ser Pro Glu Arg Glu Thr Phe
            275                 280                 285
Ser Cys His Trp Thr Asp Glu Val His His Gly Thr Lys Asn Leu Gly
        290                 295                 300
Pro Ile Gln Leu Phe Tyr Thr Arg Arg Asn Thr Gln Glu Trp Thr Gln
305                 310                 315                 320
Glu Trp Lys Glu Cys Pro Asp Tyr Val Ser Ala Gly Glu Asn Ser Cys
                325                 330                 335
Tyr Phe Asn Ser Ser Phe Thr Ser Ile Trp Ile Pro Tyr Cys Ile Lys
                340                 345                 350
Leu Thr Ser Asn Gly Gly Thr Val Asp Glu Lys Cys Phe Ser Val Asp
            355                 360                 365
Glu Ile Val Gln Pro Asp Pro Pro Ile Ala Leu Asn Trp Thr Leu Leu
        370                 375                 380
Asn Val Ser Leu Thr Gly Ile His Ala Asp Ile Gln Val Arg Trp Glu
385                 390                 395                 400
Ala Pro Arg Asn Ala Asp Ile Gln Lys Gly Trp Met Val Leu Glu Tyr
                405                 410                 415
Glu Leu Gln Tyr Lys Glu Val Asn Glu Thr Lys Trp Lys Met Met Asp
            420                 425                 430
Pro Ile Leu Thr Thr Ser Val Pro Val Tyr Ser Leu Lys Val Asp Lys
            435                 440                 445
Glu Tyr Glu Val Arg Val Arg Ser Lys Gln Arg Asn Ser Gly Asn Tyr
    450                 455                 460
```

```
Gly Glu Phe Ser Glu Val Leu Tyr Val Thr Leu Pro Gln Met Ser Gln
465                 470                 475                 480

Lys Leu Phe Glu

<210> SEQ ID NO 6
<211> LENGTH: 458
<212> TYPE: PRT
<213> ORGANISM: Artificial
<220> FEATURE:
<223> OTHER INFORMATION: growth hormone/receptor fusion

<400> SEQUENCE: 6

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
        115                 120                 125

Glu Asp Gly Ser Pro Arg Thr Gly Gln Ile Phe Lys Gln Thr Tyr Ser
130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe Gly
            180                 185                 190

Gly Arg Gly Gly Gly Gly Ser Gly Gly Gly Gly Ser Gly Gly Gly Gly
        195                 200                 205

Ser Gly Gly Gly Gly Ser Glu Phe Phe Ser Gly Ser Glu Ala Thr Ala
    210                 215                 220

Ala Ile Leu Ser Arg Ala Pro Trp Ser Leu Gln Ser Val Asn Pro Gly
225                 230                 235                 240

Leu Lys Thr Asn Ser Ser Lys Glu Pro Lys Phe Thr Lys Cys Arg Ser
                245                 250                 255

Pro Glu Arg Glu Thr Phe Ser Cys His Trp Thr Asp Glu Val His His
            260                 265                 270

Gly Thr Lys Asn Leu Gly Pro Ile Gln Leu Phe Tyr Thr Arg Arg Asn
        275                 280                 285

Thr Gln Glu Trp Thr Gln Glu Trp Lys Glu Cys Pro Asp Tyr Val Ser
290                 295                 300

Ala Gly Glu Asn Ser Cys Tyr Phe Asn Ser Ser Phe Thr Ser Ile Trp
305                 310                 315                 320

Ile Pro Tyr Cys Ile Lys Leu Thr Ser Asn Gly Gly Thr Val Asp Glu
                325                 330                 335

Lys Cys Phe Ser Val Asp Glu Ile Val Gln Pro Asp Pro Pro Ile Ala
            340                 345                 350
```

```
Leu Asn Trp Thr Leu Leu Asn Val Ser Leu Thr Gly Ile His Ala Asp
            355                 360                 365
Ile Gln Val Arg Trp Glu Ala Pro Arg Asn Ala Asp Ile Gln Lys Gly
        370                 375                 380
Trp Met Val Leu Glu Tyr Glu Leu Gln Tyr Lys Glu Val Asn Glu Thr
385                 390                 395                 400
Lys Trp Lys Met Met Asp Pro Ile Leu Thr Thr Ser Val Pro Val Tyr
                405                 410                 415
Ser Leu Lys Val Asp Lys Glu Tyr Glu Val Arg Val Arg Ser Lys Gln
            420                 425                 430
Arg Asn Ser Gly Asn Tyr Gly Glu Phe Ser Glu Val Leu Tyr Val Thr
        435                 440                 445
Leu Pro Gln Met Ser Gln Lys Leu Phe Glu
    450                 455

<210> SEQ ID NO 7
<211> LENGTH: 480
<212> TYPE: PRT
<213> ORGANISM: Artificial
<220> FEATURE:
<223> OTHER INFORMATION: growth hormone/receptor fusion

<400> SEQUENCE: 7

Met Ala Thr Gly Ser Arg Thr Ser Leu Leu Leu Ala Phe Gly Leu Leu
1               5                   10                  15
Cys Leu Pro Trp Leu Gln Glu Gly Ser Ala Phe Pro Thr Ile Pro Leu
            20                  25                  30
Ser Arg Leu Phe Asp Asn Ala Met Leu Arg Ala His Arg Leu His Gln
        35                  40                  45
Leu Ala Phe Asp Thr Tyr Gln Glu Phe Glu Glu Ala Tyr Ile Pro Lys
    50                  55                  60
Glu Gln Lys Tyr Ser Phe Leu Gln Asn Pro Gln Thr Ser Leu Cys Phe
65                  70                  75                  80
Ser Glu Ser Ile Pro Thr Pro Ser Asn Arg Glu Glu Thr Gln Gln Lys
            85                  90                  95
Ser Asn Leu Glu Leu Leu Arg Ile Ser Leu Leu Leu Ile Gln Ser Trp
        100                 105                 110
Leu Glu Pro Val Gln Phe Leu Arg Ser Val Phe Ala Asn Ser Leu Val
    115                 120                 125
Tyr Gly Ala Ser Asp Ser Asn Val Tyr Asp Leu Leu Lys Asp Leu Glu
130                 135                 140
Glu Gly Ile Gln Thr Leu Met Gly Arg Leu Glu Asp Gly Ser Pro Arg
145                 150                 155                 160
Thr Gly Gln Ile Phe Lys Gln Thr Tyr Ser Lys Phe Asp Thr Asn Ser
                165                 170                 175
His Asn Asp Asp Ala Leu Leu Lys Asn Tyr Gly Leu Leu Tyr Cys Phe
            180                 185                 190
Arg Lys Asp Met Asp Lys Val Glu Thr Phe Leu Arg Ile Val Gln Cys
        195                 200                 205
Arg Ser Val Glu Gly Ser Cys Gly Phe Gly Gly Arg Gly Gly Gly Gly
    210                 215                 220
Ser Gly Gly Gly Gly Ser Gly Gly Gly Gly Ser Gly Gly Gly Gly Ser
225                 230                 235                 240
Glu Phe Phe Ser Gly Ser Glu Ala Thr Ala Ala Ile Leu Ser Arg Ala
                245                 250                 255
```

```
Pro Trp Ser Leu Gln Ser Val Asn Pro Gly Leu Lys Thr Asn Ser Ser
                260                 265                 270
Lys Glu Pro Lys Phe Thr Lys Cys Arg Ser Pro Glu Arg Glu Thr Phe
            275                 280                 285
Ser Cys His Trp Thr Asp Glu Val His His Gly Thr Lys Asn Leu Gly
        290                 295                 300
Pro Ile Gln Leu Phe Tyr Thr Arg Arg Asn Thr Gln Glu Trp Thr Gln
305                 310                 315                 320
Glu Trp Lys Glu Cys Pro Asp Tyr Val Ser Ala Gly Glu Asn Ser Cys
                325                 330                 335
Tyr Phe Asn Ser Ser Phe Thr Ser Ile Trp Ile Pro Tyr Cys Ile Lys
            340                 345                 350
Leu Thr Ser Asn Gly Gly Thr Val Asp Glu Lys Cys Phe Ser Val Asp
        355                 360                 365
Glu Ile Val Gln Pro Asp Pro Pro Ile Ala Leu Asn Trp Thr Leu Leu
370                 375                 380
Asn Val Ser Leu Thr Gly Ile His Ala Asp Ile Gln Val Arg Trp Glu
385                 390                 395                 400
Ala Pro Arg Asn Ala Asp Ile Gln Lys Gly Trp Met Val Leu Glu Tyr
                405                 410                 415
Glu Leu Gln Tyr Lys Glu Val Asn Glu Thr Lys Trp Lys Met Met Asp
            420                 425                 430
Pro Ile Leu Thr Thr Ser Val Pro Val Tyr Ser Leu Lys Val Asp Lys
        435                 440                 445
Glu Tyr Glu Val Arg Val Arg Ser Lys Gln Arg Asn Ser Gly Asn Tyr
450                 455                 460
Gly Glu Phe Ser Glu Val Leu Tyr Val Thr Leu Pro Gln Met Ser Gln
465                 470                 475                 480

<210> SEQ ID NO 8
<211> LENGTH: 454
<212> TYPE: PRT
<213> ORGANISM: Artificial
<220> FEATURE:
<223> OTHER INFORMATION: growth hormone/receptor fusion

<400> SEQUENCE: 8

Phe Pro Thr Ile Pro Leu Ser Arg Leu Phe Asp Asn Ala Met Leu Arg
1               5                   10                  15
Ala His Arg Leu His Gln Leu Ala Phe Asp Thr Tyr Gln Glu Phe Glu
                20                  25                  30
Glu Ala Tyr Ile Pro Lys Glu Gln Lys Tyr Ser Phe Leu Gln Asn Pro
            35                  40                  45
Gln Thr Ser Leu Cys Phe Ser Glu Ser Ile Pro Thr Pro Ser Asn Arg
        50                  55                  60
Glu Glu Thr Gln Gln Lys Ser Asn Leu Glu Leu Leu Arg Ile Ser Leu
65                  70                  75                  80
Leu Leu Ile Gln Ser Trp Leu Glu Pro Val Gln Phe Leu Arg Ser Val
                85                  90                  95
Phe Ala Asn Ser Leu Val Tyr Gly Ala Ser Asp Ser Asn Val Tyr Asp
            100                 105                 110
Leu Leu Lys Asp Leu Glu Glu Gly Ile Gln Thr Leu Met Gly Arg Leu
        115                 120                 125
Glu Asp Gly Ser Pro Arg Thr Gly Gln Ile Phe Lys Gln Thr Tyr Ser
130                 135                 140
```

-continued

```
Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
            165                 170                 175

Leu Arg Ile Val Gln Cys Arg Ser Val Glu Gly Ser Cys Gly Phe Gly
        180                 185                 190

Gly Arg Gly Gly Gly Gly Ser Gly Gly Gly Ser Gly Gly Gly Gly
    195                 200                 205

Ser Gly Gly Gly Ser Glu Phe Phe Ser Gly Ser Glu Ala Thr Ala
210                 215                 220

Ala Ile Leu Ser Arg Ala Pro Trp Ser Leu Gln Ser Val Asn Pro Gly
225                 230                 235                 240

Leu Lys Thr Asn Ser Ser Lys Glu Pro Lys Phe Thr Lys Cys Arg Ser
            245                 250                 255

Pro Glu Arg Glu Thr Phe Ser Cys His Trp Thr Asp Glu Val His His
        260                 265                 270

Gly Thr Lys Asn Leu Gly Pro Ile Gln Leu Phe Tyr Thr Arg Arg Asn
    275                 280                 285

Thr Gln Glu Trp Thr Gln Glu Trp Lys Glu Cys Pro Asp Tyr Val Ser
290                 295                 300

Ala Gly Glu Asn Ser Cys Tyr Phe Asn Ser Ser Phe Thr Ser Ile Trp
305                 310                 315                 320

Ile Pro Tyr Cys Ile Lys Leu Thr Ser Asn Gly Gly Thr Val Asp Glu
            325                 330                 335

Lys Cys Phe Ser Val Asp Glu Ile Val Gln Pro Asp Pro Pro Ile Ala
        340                 345                 350

Leu Asn Trp Thr Leu Leu Asn Val Ser Leu Thr Gly Ile His Ala Asp
    355                 360                 365

Ile Gln Val Arg Trp Glu Ala Pro Arg Asn Ala Asp Ile Gln Lys Gly
370                 375                 380

Trp Met Val Leu Glu Tyr Glu Leu Gln Tyr Lys Glu Val Asn Glu Thr
385                 390                 395                 400

Lys Trp Lys Met Met Asp Pro Ile Leu Thr Thr Ser Val Pro Val Tyr
            405                 410                 415

Ser Leu Lys Val Asp Lys Glu Tyr Glu Val Arg Val Arg Ser Lys Gln
        420                 425                 430

Arg Asn Ser Gly Asn Tyr Gly Glu Phe Ser Glu Val Leu Tyr Val Thr
    435                 440                 445

Leu Pro Gln Met Ser Gln
    450

<210> SEQ ID NO 9
<211> LENGTH: 480
<212> TYPE: PRT
<213> ORGANISM: Artificial
<220> FEATURE:
<223> OTHER INFORMATION: growth hormone/receptor fusion

<400> SEQUENCE: 9

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala His Arg Leu His Gln
        35                  40                  45
```

-continued

```
Leu Ala Phe Asp Thr Tyr Gln Glu Phe Glu Ala Tyr Ile Pro Lys
 50                  55                  60

Glu Gln Lys Tyr Ser Phe Leu Gln Asn Pro Gln Thr Ser Leu Cys Phe
 65                  70                  75                  80

Ser Glu Ser Ile Pro Thr Pro Ser Asn Arg Glu Glu Thr Gln Gln Lys
                 85                  90                  95

Ser Asn Leu Glu Leu Leu Arg Ile Ser Leu Leu Leu Ile Gln Ser Trp
                100                 105                 110

Leu Glu Pro Val Gln Phe Leu Arg Ser Val Phe Ala Asn Ser Leu Val
            115                 120                 125

Tyr Gly Ala Ser Asp Ser Asn Val Tyr Asp Leu Lys Asp Leu Glu
130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
            195                 200                 205

Arg Ser Val Glu Gly Ser Cys Gly Phe Gly Gly Gly Ser Gly Gly
210                 215                 220

Gly Gly Ser Gly Gly Gly Ser Gly Gly Gly Ser Gly Gly
225                 230                 235                 240

Gly Ser Phe Ser Gly Ser Glu Ala Thr Ala Ile Leu Ser Arg Ala
            245                 250                 255

Pro Trp Ser Leu Gln Ser Val Asn Pro Gly Leu Lys Thr Asn Ser Ser
            260                 265                 270

Lys Glu Pro Lys Phe Thr Lys Cys Arg Ser Pro Glu Arg Glu Thr Phe
275                 280                 285

Ser Cys His Trp Thr Asp Glu Val His His Gly Thr Lys Asn Leu Gly
    290                 295                 300

Pro Ile Gln Leu Phe Tyr Thr Arg Arg Asn Thr Gln Glu Trp Thr Gln
305                 310                 315                 320

Glu Trp Lys Glu Cys Pro Asp Tyr Val Ser Ala Gly Glu Asn Ser Cys
                325                 330                 335

Tyr Phe Asn Ser Ser Phe Thr Ser Ile Trp Ile Pro Tyr Cys Ile Lys
                340                 345                 350

Leu Thr Ser Asn Gly Gly Thr Val Asp Glu Lys Cys Phe Ser Val Asp
            355                 360                 365

Glu Ile Val Gln Pro Asp Pro Pro Ile Ala Leu Asn Trp Thr Leu Leu
            370                 375                 380

Asn Val Ser Leu Thr Gly Ile His Ala Asp Ile Gln Val Arg Trp Glu
385                 390                 395                 400

Ala Pro Arg Asn Ala Asp Ile Gln Lys Gly Trp Met Val Leu Glu Tyr
                405                 410                 415

Glu Leu Gln Tyr Lys Glu Val Asn Glu Thr Lys Trp Lys Met Met Asp
            420                 425                 430

Pro Ile Leu Thr Thr Ser Val Pro Val Tyr Ser Leu Lys Val Asp Lys
            435                 440                 445

Glu Tyr Glu Val Arg Val Arg Ser Lys Gln Arg Asn Ser Gly Asn Tyr
            450                 455                 460

Gly Glu Phe Ser Glu Val Leu Tyr Val Thr Leu Pro Gln Met Ser Gln
465                 470                 475                 480
```

<210> SEQ ID NO 10
<211> LENGTH: 454
<212> TYPE: PRT
<213> ORGANISM: Artificial
<220> FEATURE:
<223> OTHER INFORMATION: growth hormone/receptor fusion

<400> SEQUENCE: 10

```
Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
        115                 120                 125

Glu Asp Gly Ser Pro Arg Thr Gly Gln Ile Phe Lys Gln Thr Tyr Ser
    130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe Gly
            180                 185                 190

Gly Gly Gly Ser Gly Gly Gly Gly Ser Gly Gly Gly Gly Ser Gly Gly
        195                 200                 205

Gly Gly Ser Gly Gly Gly Gly Ser Phe Ser Gly Ser Glu Ala Thr Ala
    210                 215                 220

Ala Ile Leu Ser Arg Ala Pro Trp Ser Leu Gln Ser Val Asn Pro Gly
225                 230                 235                 240

Leu Lys Thr Asn Ser Ser Lys Glu Pro Lys Phe Thr Lys Cys Arg Ser
                245                 250                 255

Pro Glu Arg Glu Thr Phe Ser Cys His Trp Thr Asp Glu Val His His
            260                 265                 270

Gly Thr Lys Asn Leu Gly Pro Ile Gln Leu Phe Tyr Thr Arg Arg Asn
        275                 280                 285

Thr Gln Glu Trp Thr Gln Glu Trp Lys Glu Cys Pro Asp Tyr Val Ser
    290                 295                 300

Ala Gly Glu Asn Ser Cys Tyr Phe Asn Ser Ser Phe Thr Ser Ile Trp
305                 310                 315                 320

Ile Pro Tyr Cys Ile Lys Leu Thr Ser Asn Gly Gly Thr Val Asp Glu
                325                 330                 335

Lys Cys Phe Ser Val Asp Glu Ile Val Gln Pro Asp Pro Pro Ile Ala
            340                 345                 350

Leu Asn Trp Thr Leu Leu Asn Val Ser Leu Thr Gly Ile His Ala Asp
        355                 360                 365
```

```
Ile Gln Val Arg Trp Glu Ala Pro Arg Asn Ala Asp Ile Gln Lys Gly
        370                 375                 380

Trp Met Val Leu Glu Tyr Glu Leu Gln Tyr Lys Glu Val Asn Glu Thr
385                 390                 395                 400

Lys Trp Lys Met Met Asp Pro Ile Leu Thr Thr Ser Val Pro Val Tyr
                405                 410                 415

Ser Leu Lys Val Asp Lys Glu Tyr Glu Val Arg Val Arg Ser Lys Gln
            420                 425                 430

Arg Asn Ser Gly Asn Tyr Gly Glu Phe Ser Glu Val Leu Tyr Val Thr
        435                 440                 445

Leu Pro Gln Met Ser Gln
    450

<210> SEQ ID NO 11
<211> LENGTH: 455
<212> TYPE: PRT
<213> ORGANISM: Artificial
<220> FEATURE:
<223> OTHER INFORMATION: growth hormone/receptor fusion

<400> SEQUENCE: 11

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala His Arg Leu His Gln
        35                  40                  45

Leu Ala Phe Asp Thr Tyr Gln Glu Phe Glu Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe Phe Ser Gly Ser Glu Ala Thr
    210                 215                 220

Ala Ala Ile Leu Ser Arg Ala Pro Trp Ser Leu Gln Ser Val Asn Pro
225                 230                 235                 240

Gly Leu Lys Thr Asn Ser Ser Lys Glu Pro Lys Phe Thr Lys Cys Arg
                245                 250                 255

Ser Pro Glu Arg Glu Thr Phe Ser Cys His Trp Thr Asp Glu Val His
            260                 265                 270
```

```
His Gly Thr Lys Asn Leu Gly Pro Ile Gln Leu Phe Tyr Thr Arg Arg
            275                 280                 285

Asn Thr Gln Glu Trp Thr Gln Glu Trp Lys Glu Cys Pro Asp Tyr Val
290                 295                 300

Ser Ala Gly Glu Asn Ser Cys Tyr Phe Asn Ser Ser Phe Thr Ser Ile
305                 310                 315                 320

Trp Ile Pro Tyr Cys Ile Lys Leu Thr Ser Asn Gly Gly Thr Val Asp
                325                 330                 335

Glu Lys Cys Phe Ser Val Asp Glu Ile Val Gln Pro Asp Pro Pro Ile
            340                 345                 350

Ala Leu Asn Trp Thr Leu Leu Asn Val Ser Leu Thr Gly Ile His Ala
            355                 360                 365

Asp Ile Gln Val Arg Trp Glu Ala Pro Arg Asn Ala Asp Ile Gln Lys
370                 375                 380

Gly Trp Met Val Leu Glu Tyr Glu Leu Gln Tyr Lys Glu Val Asn Glu
385                 390                 395                 400

Thr Lys Trp Lys Met Met Asp Pro Ile Leu Thr Thr Ser Val Pro Val
                405                 410                 415

Tyr Ser Leu Lys Val Asp Lys Glu Tyr Glu Val Arg Val Arg Ser Lys
            420                 425                 430

Gln Arg Asn Ser Gly Asn Tyr Gly Glu Phe Ser Glu Val Leu Tyr Val
            435                 440                 445

Thr Leu Pro Gln Met Ser Gln
            450                 455

<210> SEQ ID NO 12
<211> LENGTH: 429
<212> TYPE: PRT
<213> ORGANISM: Artificial
<220> FEATURE:
<223> OTHER INFORMATION: growth hormone/receptor fusion

<400> SEQUENCE: 12

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
        115                 120                 125

Glu Asp Gly Ser Pro Arg Thr Gly Gln Ile Phe Lys Gln Thr Tyr Ser
    130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175
```

```
                                     -continued
Leu Arg Ile Val Gln Cys Arg Ser Val Glu Gly Ser Cys Gly Phe Phe
            180                 185                 190

Ser Gly Ser Glu Ala Thr Ala Ala Ile Leu Ser Arg Ala Pro Trp Ser
        195                 200                 205

Leu Gln Ser Val Asn Pro Gly Leu Lys Thr Asn Ser Ser Lys Glu Pro
    210                 215                 220

Lys Phe Thr Lys Cys Arg Ser Pro Glu Arg Glu Thr Phe Ser Cys His
225                 230                 235                 240

Trp Thr Asp Glu Val His His Gly Thr Lys Asn Leu Gly Pro Ile Gln
                245                 250                 255

Leu Phe Tyr Thr Arg Arg Asn Thr Gln Glu Trp Thr Gln Glu Trp Lys
                260                 265                 270

Glu Cys Pro Asp Tyr Val Ser Ala Gly Glu Asn Ser Cys Tyr Phe Asn
                275                 280                 285

Ser Ser Phe Thr Ser Ile Trp Ile Pro Tyr Cys Ile Lys Leu Thr Ser
        290                 295                 300

Asn Gly Gly Thr Val Asp Glu Lys Cys Phe Ser Val Asp Glu Ile Val
305                 310                 315                 320

Gln Pro Asp Pro Pro Ile Ala Leu Asn Trp Thr Leu Leu Asn Val Ser
                325                 330                 335

Leu Thr Gly Ile His Ala Asp Ile Gln Val Arg Trp Glu Ala Pro Arg
                340                 345                 350

Asn Ala Asp Ile Gln Lys Gly Trp Met Val Leu Glu Tyr Glu Leu Gln
                355                 360                 365

Tyr Lys Glu Val Asn Glu Thr Lys Trp Lys Met Met Asp Pro Ile Leu
    370                 375                 380

Thr Thr Ser Val Pro Val Tyr Ser Leu Lys Val Asp Lys Glu Tyr Glu
385                 390                 395                 400

Val Arg Val Arg Ser Lys Gln Arg Asn Ser Gly Asn Tyr Gly Glu Phe
                405                 410                 415

Ser Glu Val Leu Tyr Val Thr Leu Pro Gln Met Ser Gln
                420                 425
```